(12) United States Patent
Tomsovic et al.

(10) Patent No.: US 7,069,970 B2
(45) Date of Patent: Jul. 4, 2006

(54) APPARATUS FOR FORMING A LAP SEAM

(75) Inventors: Charles Robert Tomsovic, Omro, WI (US); Joseph Daniel Coenen, Kaukauna, WI (US); David Albert Maxton, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 422 days.

(21) Appl. No.: 10/408,546

(22) Filed: Apr. 3, 2003

(65) Prior Publication Data

US 2003/0205312 A1   Nov. 6, 2003

Related U.S. Application Data

(62) Division of application No. 09/858,212, filed on May 15, 2001, now Pat. No. 6,565,691.

(60) Provisional application No. 60/204,479, filed on May 16, 2000.

(51) Int. Cl.
   *B29C 65/78* (2006.01)

(52) U.S. Cl. ............... 156/444; 156/445; 156/446; 156/457; 156/465; 156/467; 493/418; 493/436

(58) Field of Classification Search .......... 156/381, 156/382, 443, 444, 445, 446, 457, 459, 461, 156/463, 465, 466, 156, 201, 203, 204, 217, 156/218, 467, 544; 493/393, 405, 408, 417, 493/436, 447, 450, 455, 456; 270/41; 29/421.1, 29/467
See application file for complete search history.

(56) References Cited

U.S. PATENT DOCUMENTS

| | | | |
|---|---|---|---|
| 1,912,466 A | 6/1933 | Remington | |
| 1,912,724 A | 6/1933 | Remington | |
| 2,037,561 A | 4/1936 | Blosser et al. | |
| 2,714,230 A | 8/1955 | Young | |
| 3,116,920 A | 1/1964 | Geer et al. | |
| 3,502,322 A | 3/1970 | Cran | |
| 3,632,030 A | 1/1972 | Cohn et al. | |
| 3,808,767 A | 5/1974 | Reid | |
| 3,870,292 A | 3/1975 | Bradley | |
| 3,874,043 A | 4/1975 | Holm | |
| 3,918,706 A | 11/1975 | Craft | |
| 3,994,486 A | 11/1976 | Nystrand | |
| 4,017,064 A | 4/1977 | Crawford et al. | |
| 4,018,432 A | 4/1977 | Frick | |

(Continued)

FOREIGN PATENT DOCUMENTS

EP    0 217 032 A2    4/1987

(Continued)

*Primary Examiner*—Gladys J P Corcoran
(74) *Attorney, Agent, or Firm*—Thomas M. Gage; John L. Brodersen; Randall W. Fieldhack

(57) ABSTRACT

New processes and apparatus for forming lap seams and making prefastened disposable absorbent articles are disclosed. The apparatus can include an interior folding mechanism adapted to position a first panel in an interior position and an exterior folding mechanism adapted to position a second panel in an exterior position relative to the interior position. The interior folding mechanism can include a mandrel defining a curved peripheral surface and an interior forming shoulder in proximity to the mandrel. A fluid pressure device can establish an air flow between the mandrel and the interior forming shoulder. The forming shoulder can modify the direction of the air flow as the first panel travels in a machine direction to increasingly fold the panel over the curved peripheral surface.

25 Claims, 18 Drawing Sheets

U.S. PATENT DOCUMENTS

| | | |
|---|---|---|
| 4,053,967 A | 10/1977 | Mair |
| 4,145,763 A | 3/1979 | Abrams et al. |
| 4,170,347 A | 10/1979 | Lewis |
| 4,186,860 A | 2/1980 | Reba |
| 4,197,621 A | 4/1980 | Mair |
| 4,205,679 A | 6/1980 | Repke et al. |
| 4,279,610 A | 7/1981 | Reba |
| 4,323,534 A | 4/1982 | DesMarais |
| 4,342,413 A | 8/1982 | Reba |
| 4,402,690 A | 9/1983 | Redfern |
| 4,418,513 A | 12/1983 | Plahm |
| 4,453,709 A | 6/1984 | Reba |
| 4,479,640 A | 10/1984 | Smith |
| 4,516,760 A | 5/1985 | Stumpf |
| 4,543,154 A | 9/1985 | Reiter |
| 4,597,573 A | 7/1986 | Reba et al. |
| 4,610,680 A | 9/1986 | LaFleur |
| 4,614,512 A | 9/1986 | Capdeboscq |
| 4,615,695 A | 10/1986 | Cooper |
| 4,640,726 A | 2/1987 | Sallee et al. |
| 4,663,106 A | 5/1987 | Pomplun et al. |
| 4,663,220 A | 5/1987 | Wisneski et al. |
| 4,665,306 A | 5/1987 | Roland et al. |
| 4,699,622 A | 10/1987 | Toussant et al. |
| 4,702,468 A | 10/1987 | Pollich |
| 4,704,116 A | 11/1987 | Enloe |
| 4,710,189 A | 12/1987 | Lash |
| 4,717,375 A | 1/1988 | Lundmark |
| 4,750,442 A | 6/1988 | Keeton |
| 4,808,252 A | 2/1989 | Lash |
| 4,834,738 A | 5/1989 | Kielpikowski et al. |
| 4,865,579 A | 9/1989 | Kirby et al. |
| 4,875,668 A | 10/1989 | Spyra |
| 4,883,549 A | 11/1989 | Frost et al. |
| 4,885,853 A | 12/1989 | McCabe |
| 4,936,840 A | 6/1990 | Proxmire |
| 4,940,464 A | 7/1990 | Van Gompel et al. |
| 5,046,272 A | 9/1991 | Vogt et al. |
| 5,087,253 A | 2/1992 | Cooper |
| 5,092,863 A | 3/1992 | Schanzlin |
| 5,093,422 A | 3/1992 | Himes |
| 5,104,116 A | 4/1992 | Pohjola |
| 5,110,403 A | 5/1992 | Ehlert |
| 5,140,757 A | 8/1992 | Terada |
| 5,176,615 A | 1/1993 | Munsch |
| 5,184,555 A | 2/1993 | Quadracci et al. |
| 5,197,722 A | 3/1993 | Adamski, Jr. et al. |
| 5,199,623 A | 4/1993 | Rajala et al. |
| 5,224,405 A | 7/1993 | Pohjola |
| 5,226,992 A | 7/1993 | Morman |
| 5,300,007 A | 4/1994 | Kober |
| 5,304,599 A | 4/1994 | Himes |
| 5,330,598 A | 7/1994 | Erdman et al. |
| 5,344,691 A | 9/1994 | Hanschen et al. |
| 5,353,979 A | 10/1994 | Gartmann |
| 5,363,784 A | 11/1994 | Adamski, Jr. et al. |
| 5,370,634 A | 12/1994 | Ando et al. |
| 5,399,219 A | 3/1995 | Roessler et al. |
| 5,435,802 A | 7/1995 | Kober |
| 5,556,360 A | 9/1996 | Kober et al. |
| 5,660,666 A | 8/1997 | Dilnik et al. |
| 5,705,013 A | 1/1998 | Nease et al. |
| 5,733,401 A | 3/1998 | Linman et al. |
| 5,765,495 A | 6/1998 | Adamski, Jr. |
| 5,766,389 A | 6/1998 | Brandon et al. |
| 5,779,831 A | 7/1998 | Schmitz |
| 5,785,699 A | 7/1998 | Schmitz |
| 5,788,805 A | 8/1998 | Herrmann |
| 5,795,350 A | 8/1998 | Schmitz |
| 5,795,433 A | 8/1998 | Niedermeyer |
| 5,803,448 A | 9/1998 | Stiel et al. |
| 5,807,368 A | 9/1998 | Helmer |
| 5,830,206 A | 11/1998 | Larsson |
| 5,842,964 A | 12/1998 | Huber et al. |
| 5,855,574 A | 1/1999 | Kling et al. |
| 5,858,515 A | 1/1999 | Stokes et al. |
| 5,865,135 A | 2/1999 | Price et al. |
| 5,897,545 A | 4/1999 | Kline et al. |
| 5,904,802 A | 5/1999 | Niedermeyer |
| 5,915,319 A | 6/1999 | Price et al. |
| 5,916,203 A | 6/1999 | Brandon et al. |
| 5,919,334 A | 7/1999 | Niedermeyer |
| 5,997,981 A | 12/1999 | McCormack et al. |
| 6,022,431 A | 2/2000 | Blenke et al. |
| 6,022,432 A | 2/2000 | Elsberg et al. |
| 6,027,440 A | 2/2000 | Roth |
| 6,036,805 A | 3/2000 | McNichols |
| 6,113,717 A | 9/2000 | Vogt et al. |
| 6,287,287 B1 | 9/2001 | Elsberg |
| 6,328,725 B1 | 12/2001 | Fernfors |
| 6,395,115 B1 | 5/2002 | Popp et al. |
| 6,409,858 B1 | 6/2002 | Popp et al. |
| 6,432,243 B1 | 8/2002 | Popp et al. |
| 6,432,248 B1 | 8/2002 | Popp et al. |
| 6,447,628 B1 | 9/2002 | Couillard et al. |
| 6,461,344 B1 | 10/2002 | Widlund et al. |
| 6,481,362 B1 | 11/2002 | Hietpas et al. |
| 6,497,032 B1 | 12/2002 | Maxton et al. |
| 6,513,221 B1 | 2/2003 | Vogt et al. |
| 6,514,187 B1 | 2/2003 | Coenen et al. |
| 6,562,167 B1 | 5/2003 | Coenen et al. |
| 6,565,691 B1 | 5/2003 | Tomsovic et al. |
| 6,596,113 B1 | 7/2003 | Csida et al. |
| 2002/0002358 A1 | 1/2002 | Durrance et al. |
| 2002/0173767 A1 | 11/2002 | Popp et al. |

FOREIGN PATENT DOCUMENTS

| | | |
|---|---|---|
| EP | 0 320 989 A2 | 6/1989 |
| EP | 0 532 486 A1 | 3/1993 |
| EP | 0 631 766 A1 | 1/1995 |
| EP | 0 689 816 A2 | 1/1996 |
| EP | 0 753 292 A2 | 1/1997 |
| EP | 0 761 193 A2 | 3/1997 |
| EP | 0 800 808 A1 | 10/1997 |
| EP | 0 803 602 A1 | 10/1997 |
| EP | 0 820 747 A1 | 1/1998 |
| EP | 0 757 550 B1 | 12/1998 |
| EP | 0 934 739 A2 | 8/1999 |
| FR | 2 299 254 | 8/1976 |
| GB | 1 384 622 | 2/1975 |
| GB | 1440905 A * | 6/1976 |
| GB | 1 520 740 | 8/1978 |
| GB | 1 593 600 | 7/1981 |
| GB | 2 160 817 A | 1/1986 |
| GB | 2 288 314 A | 10/1995 |
| WO | WO 91/19613 A1 | 12/1991 |
| WO | WO 95/18589 A1 | 7/1995 |
| WO | WO 95/18591 A2 | 7/1995 |
| WO | WO 95/27462 A1 | 10/1995 |
| WO | WO 95/32639 A1 | 12/1995 |
| WO | WO 95/33618 A1 | 12/1995 |
| WO | WO 97/23180 A1 | 7/1997 |
| WO | WO 97/24098 A1 | 7/1997 |
| WO | WO 98/15248 A1 | 4/1998 |
| WO | WO 99/65441 A1 | 12/1999 |
| WO | WO 00/23025 A1 | 4/2000 |
| WO | WO 00/35395 A2 | 6/2000 |
| WO | WO 00/35398 A1 | 6/2000 |
| WO | WO 00/37009 A2 | 6/2000 |

* cited by examiner

APPARATUS FOR FORMING A LAP SEAM

This application is a divisional of application Ser. No. 09/858,212 entitled Method And Apparatus For Forming A Lap Seam and filed in the U.S. Patent and Trademark Office on May 15, 2001, now U.S. Pat. No. 6,565,691, which claims priority from provisional application Ser. No. 60/204,479 filed in the U.S. Patent and Trademark Office on May 16, 2000. The entirety of application Ser. No. 09/858,212 is hereby incorporated by reference.

BACKGROUND OF THE INVENTION

The present invention pertains to processes and apparatus for forming a lap seam, and more particularly to processes and apparatus for making prefastened disposable absorbent garments including lap seams.

Garments such as disposable absorbent garments have numerous applications including diapers, training pants, feminine care products, and adult incontinence products. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

What is lacking and needed in the art are processes and apparatus for forming lap seams such as for the manufacture of prefastened disposable absorbent garments.

SUMMARY OF THE INVENTION

In response to the above-referenced unfulfilled need in the art, new processes and apparatus for forming lap seams and making prefastened disposable absorbent articles have been discovered.

In one aspect, the invention concerns an apparatus for positioning a pair of panels in overlapping orientation. The apparatus comprises a transport system defining a machine center line, an interior folding mechanism adapted to position a first panel in an interior position, and an exterior folding mechanism adapted to position a second panel in an exterior position relative to the interior position. The interior folding mechanism comprises a mandrel transversely spaced from the machine center line and defining a curved peripheral surface, and an interior forming shoulder in proximity to the mandrel and defining an interior surface disposed toward the mandrel and an opposite exterior surface. The curved peripheral surface and the interior surface define an inner passage therebetween. A fluid pressure device is operatively associated with the inner passage and adapted to establish an air flow through the inner passage.

In another aspect, the invention concerns an apparatus for positioning first and second panels in overlapping orientation, comprising: a transport system defining a machine center line; an interior panel folding mechanism adapted to position a first panel in an interior position; and an exterior panel folding mechanism adapted to position a second panel in an exterior position relative to the interior position. The interior panel folding mechanism comprises a mandrel transversely spaced from the machine center line and defining a curved peripheral surface. The interior panel folding mechanism also comprises an interior forming shoulder defining an interior surface disposed toward the mandrel, an opposite exterior surface, a distal edge, and a head portion adjacent the distal edge and in contact with the mandrel. The curved peripheral surface and the interior surface define an inner passage therebetween, and a fluid pressure device is operatively associated with the inner passage and adapted to establish an air flow through the inner passage and against the interior surface.

In another aspect, the invention concerns an apparatus for positioning first and second panels in overlapping orientation, comprising a transport system defining a machine center line, and an interior panel folding mechanism adapted to position a first panel in an interior position. The interior panel folding mechanism comprises: a mandrel transversely spaced from the machine center line and defining a body having a curved peripheral surface, an internal mandrel chamber within the body, and an aperture through the body and in communication with the internal mandrel chamber; an interior forming shoulder in proximity to the mandrel and defining an interior surface disposed toward the mandrel and an opposite exterior surface, the curved peripheral surface and the interior surface defining an inner passage therebetween; and a fluid pressure device operatively associated with the inner passage and adapted to establish an air flow through the inner passage and into the internal mandrel chamber; and an exterior panel folding mechanism adapted to position a second panel in an exterior position relative to the interior position.

In another aspect, the invention concerns a method for forming a lap seam. The method comprises transporting first and second panels in a machine direction, where the first and second panels are discontinuous in the machine direction. The first panel is fluidly directed onto a curved peripheral surface of a mandrel as the first panel is transported in the machine direction. A second panel is positioned transversely outward from the first panel, with the first panel disposed between the curved peripheral surface and the second panel. The first and second panels are either permanently or refastenably bonded together.

In another aspect, the invention concerns a method of forming a lap seam, comprising: transporting first and second panels in a machine direction with a mandrel comprising a curved peripheral surface disposed between the panels, the first panel disposed between the curved peripheral surface and an interior surface of an interior forming shoulder, the curved peripheral surface and the interior surface defining an inner passage therebetween; establishing an air flow through the inner passage such that the first panel is fluidly directed toward the curved peripheral surface; positioning the second panel transversely outward from the first panel, with the first panel disposed between the mandrel and the second panel; and bonding the first and second panels together.

In yet another aspect, the invention concerns a method for progressively folding first and second discrete panels to form a lap seam. First and second panels are transported in a machine direction. A mandrel is introduced in proximity to the first panel. The mandrel defines a body having a curved peripheral surface. An air flow is established and directed toward the first panel at multiple machine direction positions, such that the air flow directs the first panel toward the curved peripheral surface. The method also includes modifying the direction of the air flow at downstream machine direction positions so that the air flow increasingly folds the first panel over the curved peripheral surface as the first panel is transported in the machine direction. The second panel is positioned transversely outward from the first panel, and the first and second panels are bonded together.

In still another aspect, the invention concerns a method for seaming a pant with first and second pairs of side panels, comprising: transporting a folded pant in a machine direction, the folded pant having opposite first and second waist regions in facing relation, including first side panels of the first waist region in facing relation with second side panels of the second waist region; positioning the first side panels adjacent mandrels having curved peripheral surfaces; creating air flows adjacent the first side panels to direct the first side panels toward the curved exterior surfaces; modifying the direction of the air flows at downstream machine direction positions; and bonding the respective first and second side panels together.

In another aspect, the invention concerns a method for making a pant. The method comprises providing a pant chassis defining a first waist region, a second waist region, a crotch region which extends between and interconnects the waist regions, first side panels disposed in the first waist region and second side panels disposed in the second waist region. The pant chassis is folded about a fold line extending in a lateral direction through the crotch region, thereby positioning the waist regions and respective first and second side panels in a facing relation. The folded pant chassis is transported in a machine direction with mandrels disposed between each of the facing first and second side panels, such that each first side panel is disposed between a curved peripheral surface of a mandrel and an interior surface of an interior forming shoulder. Each curved peripheral surface and each interior surface define an inner passage therebetween. An air flow is established through each inner passage such that each first side panel is fluidly directed toward a curved peripheral surface. Each second side panel is positioned transversely outward from its respective first side panel, with the first side panel disposed between the mandrel and the second side panel. The overlapping first and second side panels are bonded together.

The garments can include permanently bonded side seams or refastenable side seams. Non-refastenable seams can be formed by ultrasonic bonds, adhesive bonds, thermal bonds, sewing, or the like. Fastening components to form refastenable seams can comprise separate elements bonded to another component of the pant. Alternatively, the fastening components can comprise a portion of another element of the pant, such as the bodyside liner, the outer cover, separate side panels if employed, integral side panels if employed, a belt-type component extending transversely across the chassis if employed, or the like. Thus, unless otherwise specified, the term "fastening component" includes separate components which function as fasteners and regions of materials such as side panels, liners, outer covers or the like which function as fasteners. Moreover, a single material can define multiple fastening components to the extent that different regions of the material function as separate fasteners. The fastening components can be located on the side panels, between the side panels such as on the absorbent chassis, or a combination of the two. The fastening components can have any desired shape, such as square, rectangular, round, curved, oval, irregularly shaped, or the like. Each fastening component can comprise a single fastening element or multiple fastening elements.

The fastening components can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

A refastenable fastening system allows for easy inspection of the interior of the pant-like product. If necessary, the fastening system also allows the pant to be removed quickly and easily. This is particularly beneficial when the pant contains messy excrement.

For training pants, the caregiver can completely remove the pant-like product and replace it with a new one without having to remove the child's shoes and clothing. Refastenable or non-refastenable fastening systems may be used with a wide variety of absorbent and non-absorbent products, including training pants, swim pants, diaper pants, incontinence garments, feminine care products, health care garments, apparel for institutional, industrial and consumer use, or other garments using mechanical or adhesive fasteners.

Absorbent articles are adapted to be worn adjacent to the body of a wearer to absorb and contain various exudates discharged from the body. The absorbent articles are desirably prefastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

Particular training pants suitable for use with the present invention are disclosed in U.S. patent application Ser. No. 09/444,083, filed on Nov. 22, 1999 (corresponding to PCT application WO 00/37009 published Jun. 29, 2000) by A. Fletcher et at and titled "Absorbent Articles With Refastenable Side Seams;" now U.S. Pat. No. 6,361,711, which is incorporated herein by reference. This reference describes various materials and methods for constructing training pants. Training pants can also be constructed using the methods end apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; which are also incorporated herein by reference.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements. Lap seams as described herein can be formed with panels that are either permanently or refastenably bonded together.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rigid" describes an element or structure that assumes a generally fixed position during use, where functionality does not depend significantly on movement and/or bending.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The methods and apparatus of the present invention can be used to make a variety of garments. Examples of such garments include disposable absorbent articles such as diapers, training pants, feminine hygiene products, incontinence products, other personal care or health care garments; swim pants; athletic clothing; pants and shorts; or the like. More generally, the methods and apparatus can be used to form lap seams between any panels, including those representing completely separate webs or structures, distinct or designated portions of a connected product assemblage, or distinct or designated portions of an integral layer. For ease of explanation, the description hereafter will be in terms of methods and apparatus for making a child's training pant. In particular, the methods and apparatus will be described in terms of those for making prefastened disposable training pants as described in U.S. patent application Ser. No. 09/444,083 titled "Absorbent Articles With Refastenable Side Seams" and filed Nov. 22, 1999 by A. L. Fletcher et al. (corresponding to PCT application WO 00/37009 published Jun. 29, 2000), now U.S. Pat. No. 6,761,711, the disclosure of which is incorporated herein by reference.

Figure 1:
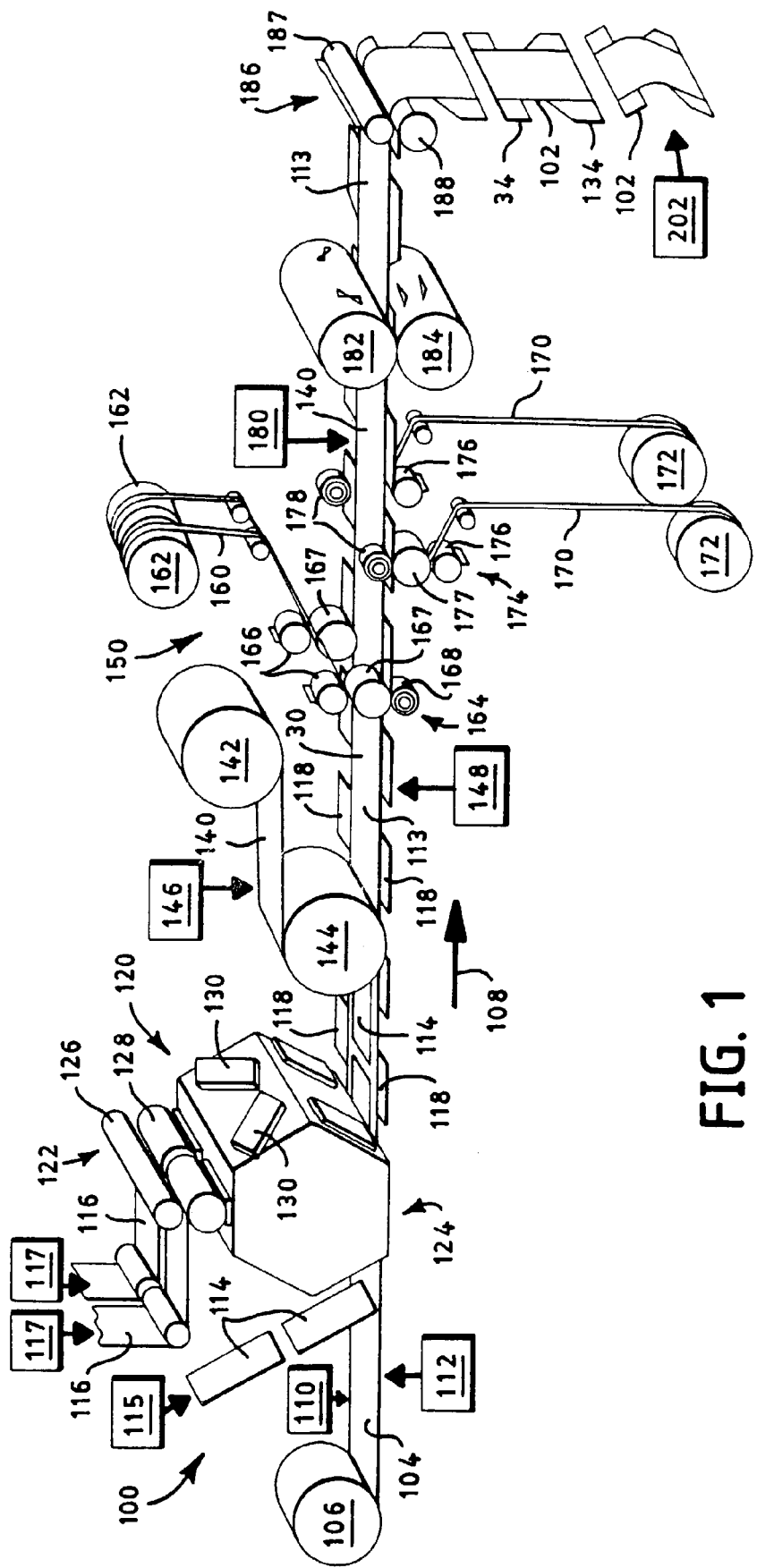
FIG. 1 is a schematic view of an exemplary embodiment of an assembly section for making garments such as training pants.
Figure 2:
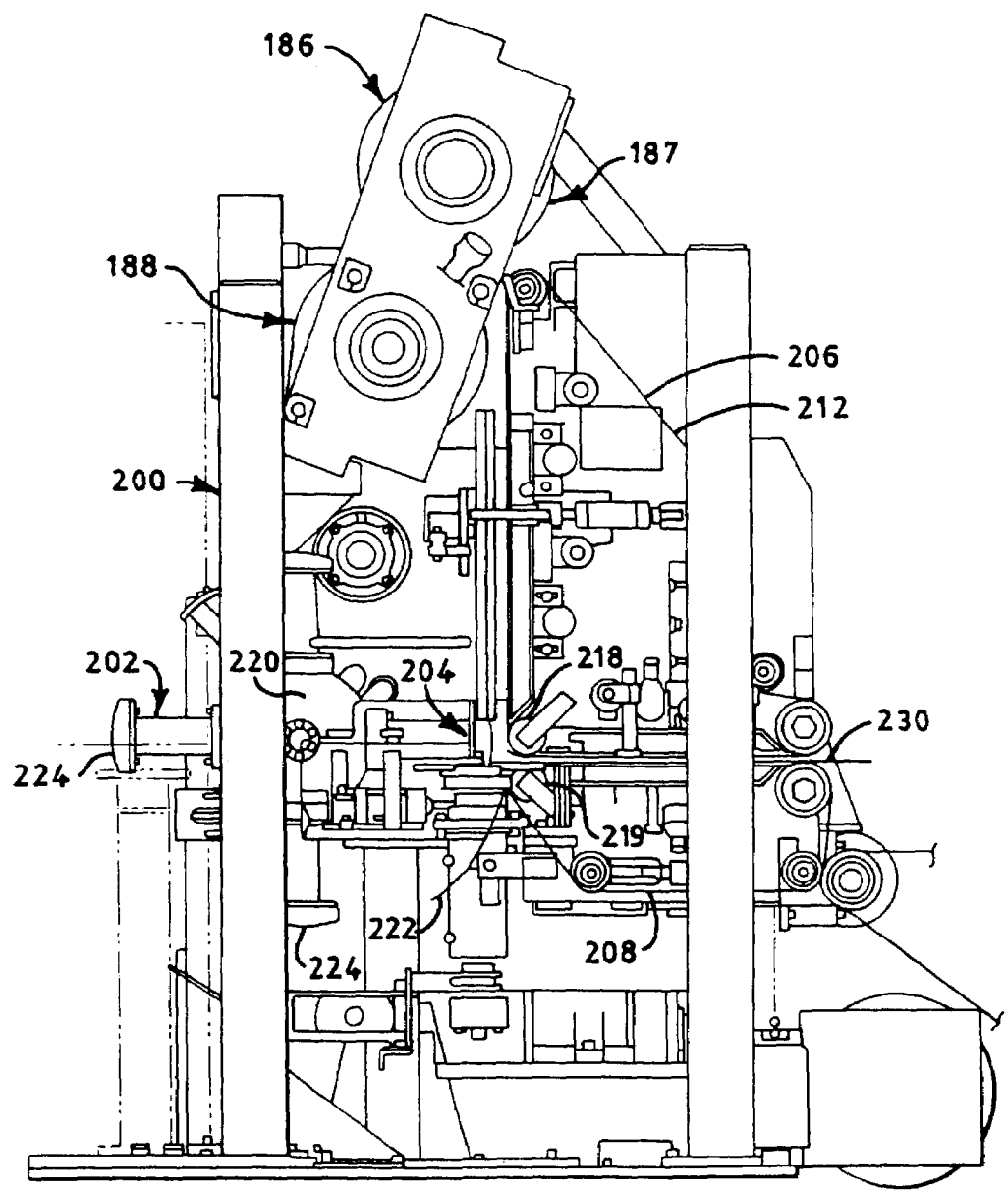
FIG. 2 is a schematic side view of an exemplary embodiment of a folding section for making garments such as training pants, the folding section following the assembly section shown in FIG. 1.
Figure 3:
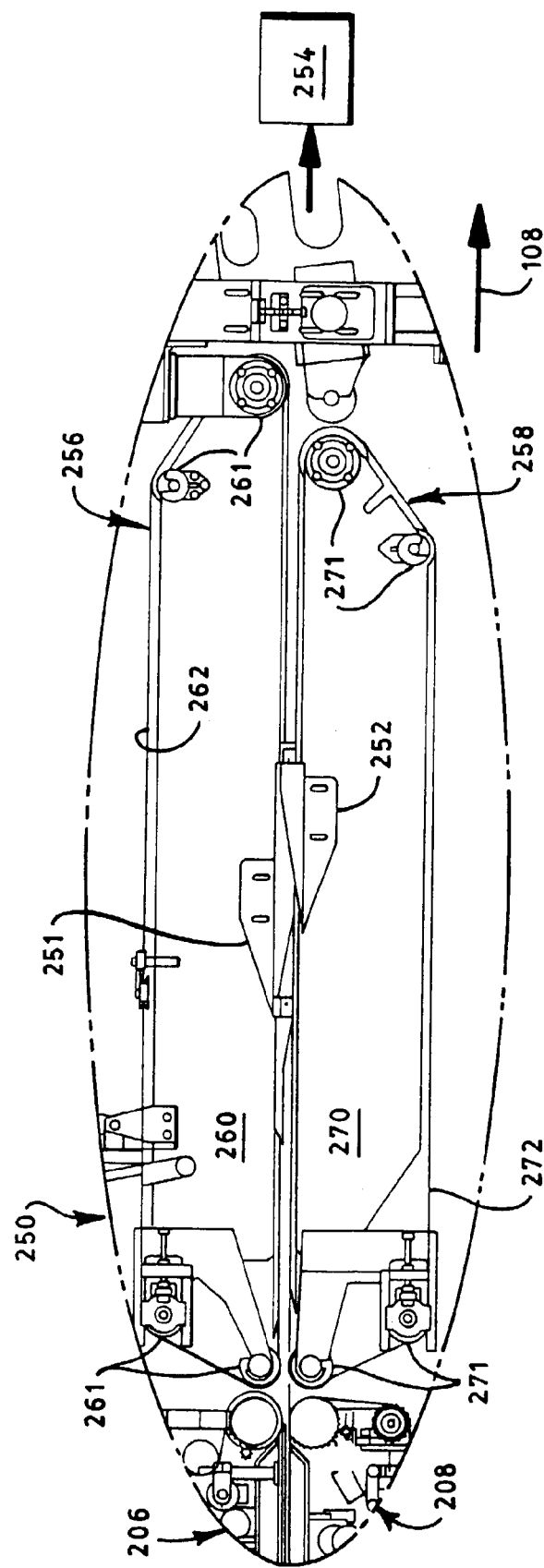
FIG. 3 is a schematic side view of one embodiment of a method and apparatus for making garments according to the present invention, the view illustrating a seaming section which follows the folding section shown in FIG. 2.

FIGS. 1–3 representatively illustrate one embodiment of a method and apparatus for making a training pant 20. The training pant 20 is illustrated separately and in a partially fastened condition in FIG. 4. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 4:
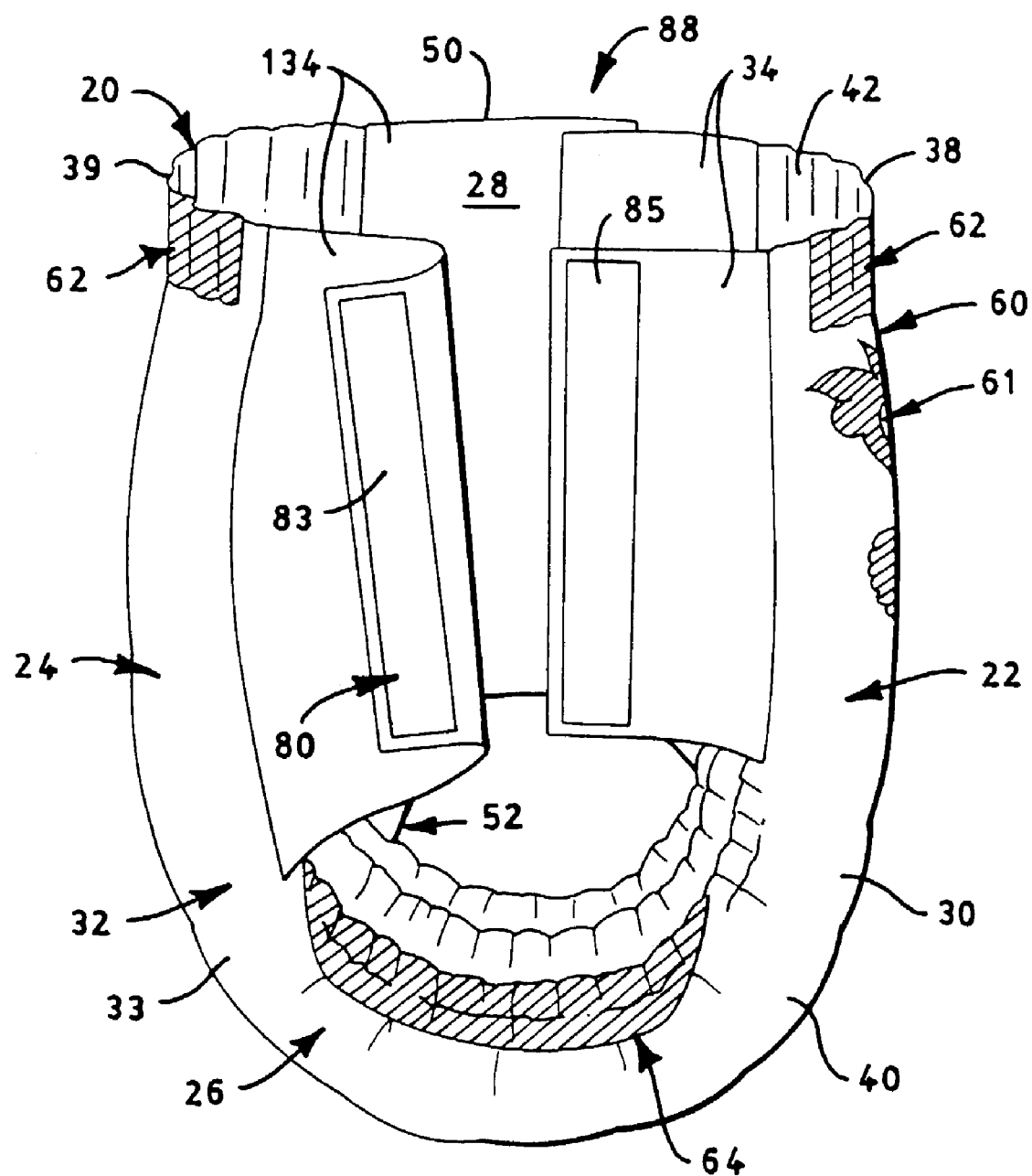
FIG. 4 illustrates a side view of a training pant made by the process and apparatus shown in FIGS. 1–3, where the fastening system is shown engaged on one side of the training pant and disengaged on the other side of the training pant.
Figure 5:
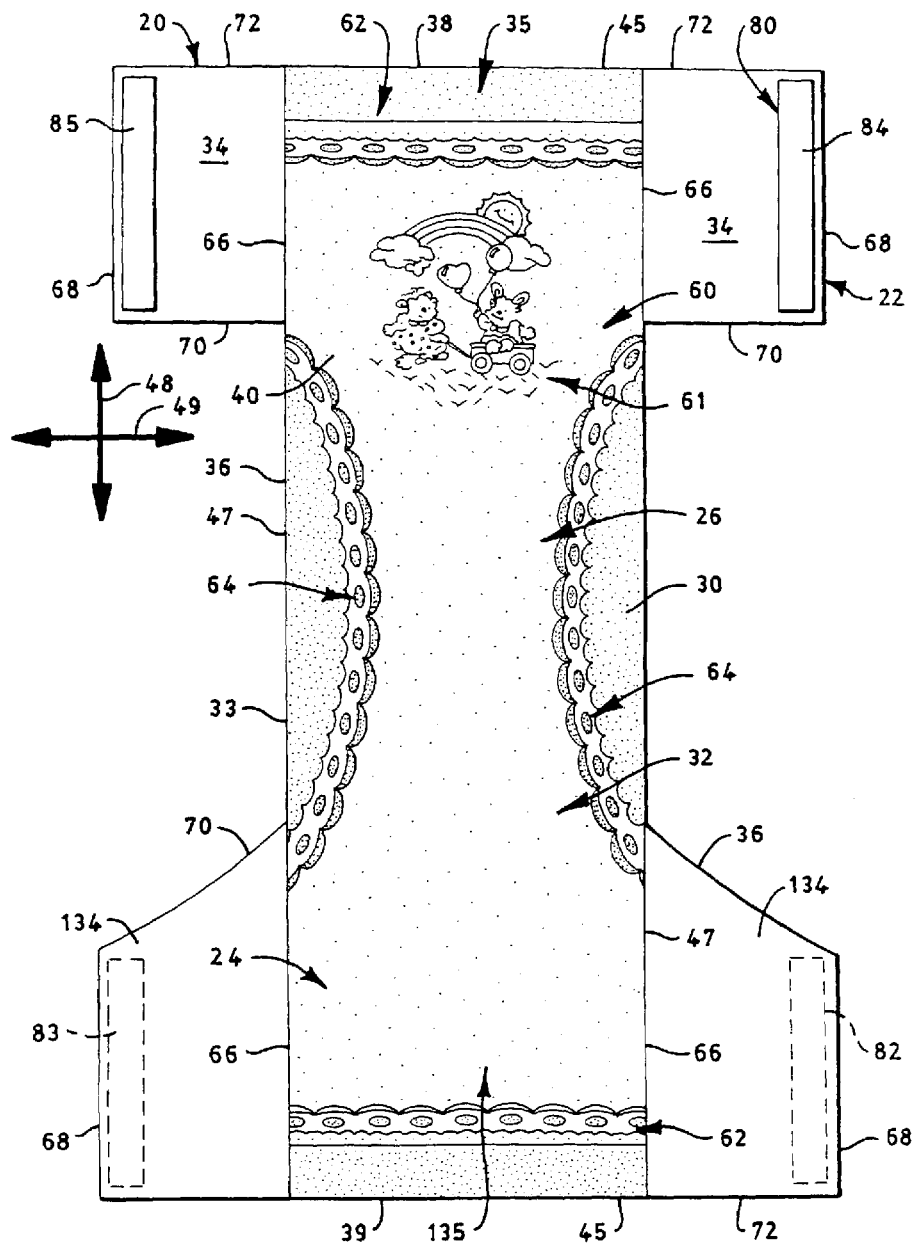
FIG. 5 illustrates a plan view of the training pant shown in FIG. 4 in an unfastened, stretched and laid flat condition, and showing the surface of the training pant that faces away from the wearer.
Figure 6:
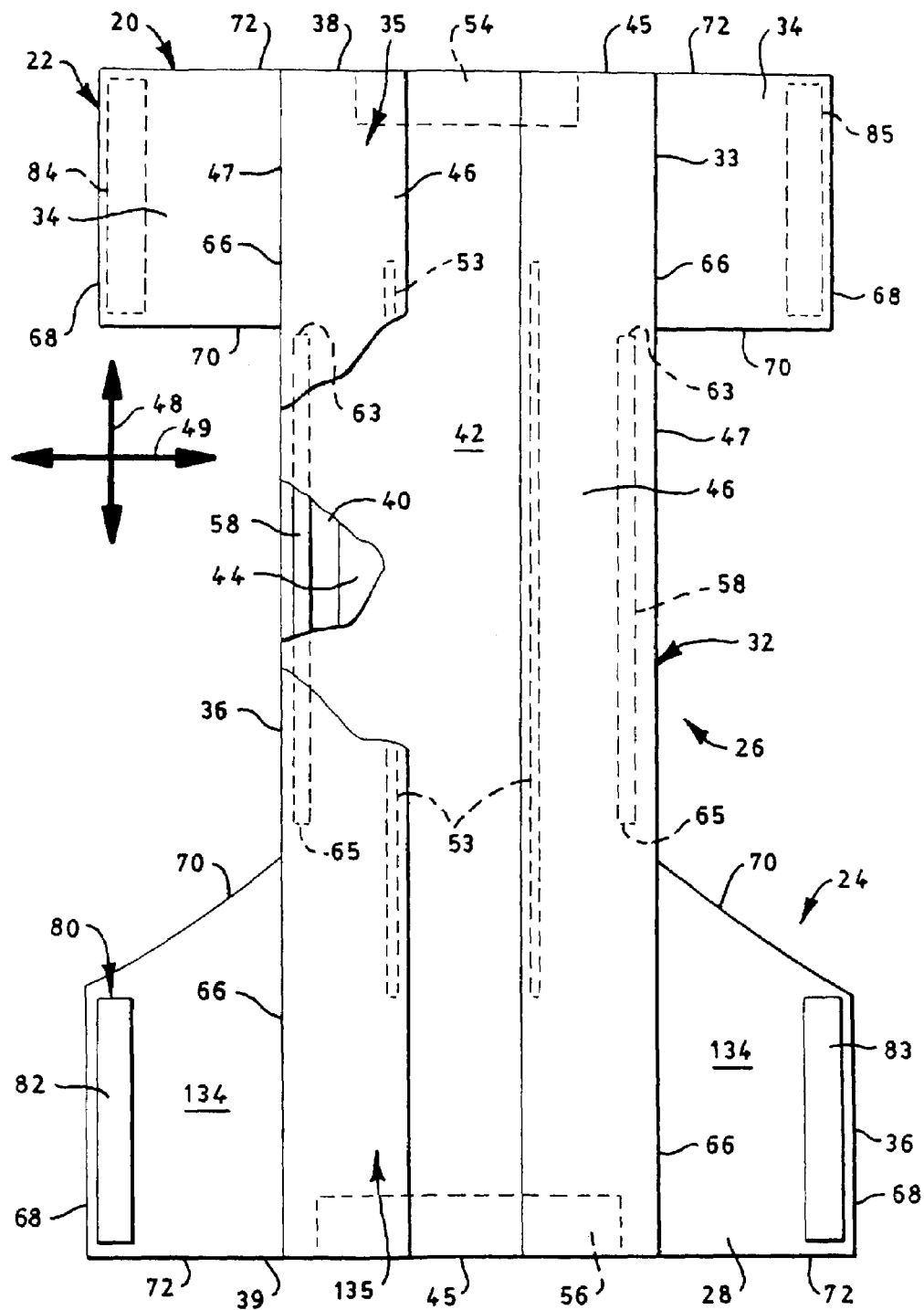
FIG. 6 illustrates a plan view similar to FIG. 5, but showing the surface of the training pant that faces the wearer when the training pant is worn, and with portions cut away to show the underlying features.

The illustrated absorbent chassis 32 comprises a composite structure 33 which can be rectangular or any other desired shape, a pair of transversely opposed front side panels 34, and a pair of transversely opposed back side panels 134. The composite structure 33 and side panels 34 and 134 may be integrally formed or comprise two or more separate elements, as shown in FIG. 4. The illustrated composite structure 33 comprises an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The illustrated composite structure 33 has opposite linear end edges 45 that form portions of the front and back waist edges 38 and 39, and opposite linear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 6) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 4 and 5, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal center line of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pant can comprise elastomeric or nonelastomeric materials.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape comprises a blend of wood pulp fluff and superabsorbent material.

One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 5 and 6.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Alternatively, the fastening components can comprise interlocking similar surface fasteners; adhesive or cohesive fastening elements such as an adhesive fastener and an adhesive-receptive landing zone or material; or the like. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also comprise any fibrous structure capable of entangling or catching hook type materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82–85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600.

With particular reference to FIG. 6, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 5, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks.

The fastening components 82–85 can be adhered to the side panels 34 and 134 by any means known to those skilled in the art such as adhesive bonds, ultrasonic bonds or thermal bonds. The fastening components can comprise separate fastening elements or can comprise distinct regions of an integral material. For example, the training pant 20 can include an integral second fastening material disposed in the front waist region 22 for refastenably connecting to the first fastening components 82 and 83 at two or more different regions, which define the second fastening components 84 and 85 (FIG. 3). In a particular embodiment, the fastening components can comprise integral portions of the waist regions. For instance, one of the elastomeric front or back side panels can function as second fastening components in that they can comprise a material that is releasably engageable with fastening components disposed in the opposite waist region.

The fastening components are desirably rectangular, although they may alternatively be square, round, oval, curved or otherwise non-rectangularly shaped. In particular embodiments, each of the fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it may be desirable in some embodiments for the front side panels 34 to be longitudinally spaced from the back side panels 134 (see FIGS. 5 and 6). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 4) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is the distance measured parallel to the transverse axis 49 between the longitudinal center lines of the fasteners, measured with the side panels 34 and 134 in an unstretched condition.

An exemplary embodiment of an assembly section 100 for making a continuous stream of partially assembled, discrete garments 102 is illustrated in FIG. 1. The specific equipment and processes used in the assembly section 100 can vary greatly depending on the specific type of garment being manufactured. The particular process and apparatus described in relation to FIG. 1 is specifically adapted to manufacture training pants 20 of the type illustrated in FIG. 4.

The various components of the training pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 1 and 2. Suitable absorbent supply mechanisms, web unwinds, conveyor systems, registration systems, drives systems, control systems and the like, for use with the present process are disclosed in U.S. Pat. No. 5,766,389 issued Jun. 16, 1998 to Brandon et al., which is incorporated herein by reference. Also, the outer cover graphics 61 are not shown in FIGS. 1 and 7.

A continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each training pant. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 1 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pant 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and married with the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream of the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

The continuously moving product assemblage 113 next advances to a fastener application station 150 where fastening components 82–85 can be bonded to the strips 118 of side panel material 116. The location of the fastening components on the composite is a function in part of the configuration of the assembly section 100. The illustrated assembly section 100 is configured so that the upwardly facing surface of the product assemblage 113 will become the outer surface 30 of the training pant 20 and the downwardly facing surface will become the inner surface 28. Moreover, the illustrated assembly section 100 is configured to produce partially assembled training pants 102 having the front waist region 22 of a leading garment connected to the back waist region 24 of a trailing garment. The process could alternatively employ any combination of different orientations. For example, the upwardly facing surface of the product assemblage could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 7:
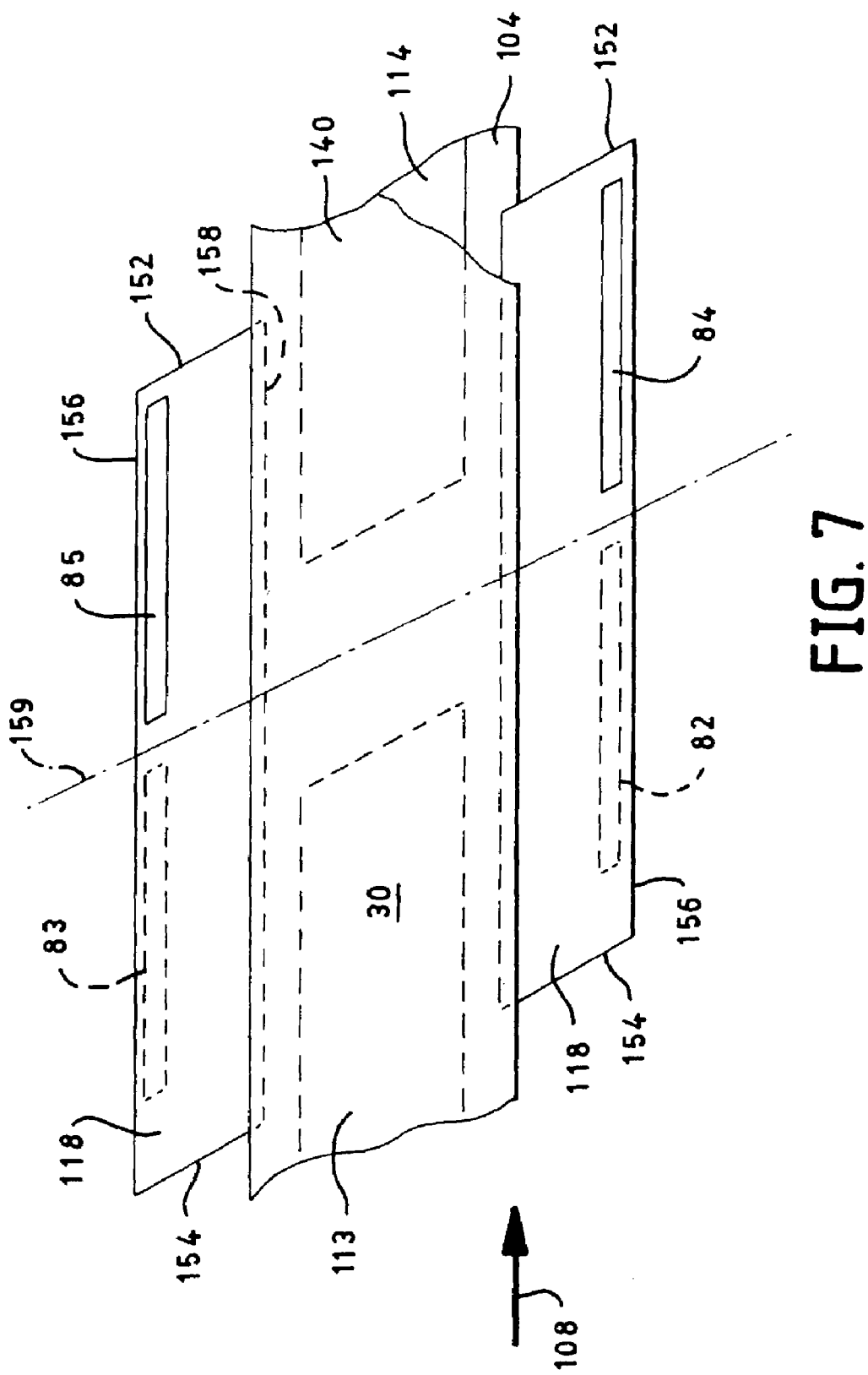
FIG. 7 illustrates a portion of a continuously moving assemblage at one point in the assembly section illustrated in FIG. 1.

The location of the fastening components 82–85 in this embodiment is best illustrated in FIG. 7, which shows a portion of the product assemblage 113 which is moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 102. Based on the illustrated orientation of the continuously moving product assemblage 113, the first fastening components 82 and 83 can be bonded to the underside of the strips 118 and the second fastening components 84 and 85 can be bonded to the top of the strips. Additionally, the first fastening components 82 and 83 can be disposed relatively closer to the trailing edge 154 and the second fastening components 84 and 85 can be disposed relatively closer to the leading edge 152. The first fastening components 82 and 83 can be spaced in the machine direction 108 from the second fastening components 84 and 85 so that the cut line 159 passes therebetween. With reference again to FIG. 1, continuous webs of second fastener material 16.0 used to form the second fastening components 84 and 85 can be provided from supply rolls 162 or other suitable sources. The second fastener materials 160 can be cut into individual second fasteners 84 and 85 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 and 83 can be provided from supply rolls 172 or other suitable sources. The first fastener materials 170 can be cut into individual first fasteners 82 and 83 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

Other arrangements can be used to attach the fastening components 82–85. For example, the fastening components can be applied to the side panel material 116 prior to uniting the side panel material with the bodyside liner material 104 and/or the outer cover material 140; the fastening components can be applied to the bodyside liner material 104 and/or outer cover material 140, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites 82, 84 and 83, 85; or the like.

After the fastening components are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location of the fastening components 82, 84 and 83, 85. Particular ultrasonic bond patterns comprising individual, circular bonds which are compatible with mechanical fastening materials are disclosed in U.S. Pat. No. 5,660,666 issued Aug. 26, 1997 to Dilnik et al., which is incorporated herein by reference. For secure attachment, it may be desirable to attach the fastening components with both adhesive and thermal bonds. Efficient arrangements for attaching the fastening components with nonadhesive bonding devices are further described in U.S. Pat. No. 6,562,167, issued May 13, 2003 to J. D. Coenen et al. and titled "Methods For Making Garments With Fastening Components," which is incorporated herein by reference. Suitable attachment adhesives are available from commercial vendors such as Findley Adhesive, Inc., Wauwatosa, Wis. U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82–85 and the side panel material 116 when the side panel material 116 reaches a particular machine direction 108 location. In one particular embodiment, the target areas correspond to portions of the fastening components 82–85 near the waist edges 38 and 39. The bonding devices 180 can be registered to provide a relatively higher degree of bonding which begins while disposed on one fastening component (such as 84 in FIG. 7), continues through the region where the product assemblage 113 will subsequently be cut (see cut line 159 in FIG. 7), and ends after being disposed on another fastening component (such as 82). Alternatively, the bonding devices 180 can destroy engaging elements of the fastening components 82–85 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 5 and 6). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled training pants moving in the direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels (FIG. 2). The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

The discrete training pants 102 can then be folded at a folding station 200 using any suitable folding mechanism 202 (FIG. 2). The training pants 102 can be folded about a fold line generally bisecting the training pants. As such, the waist regions 22 and 24 of each training pant 102 are positioned in facing relationship with the side panels 34 and 134 extending laterally outward relative to the longitudinal axis 48 of the training pant. The fold line can extend in a lateral direction through the crotch region 26 of the training pant. Desirably, each discrete training pant 102 is consistently folded about the fold line such that the front and back waist edges 38 and 39 of the training pant align with each other.

Figure 8:
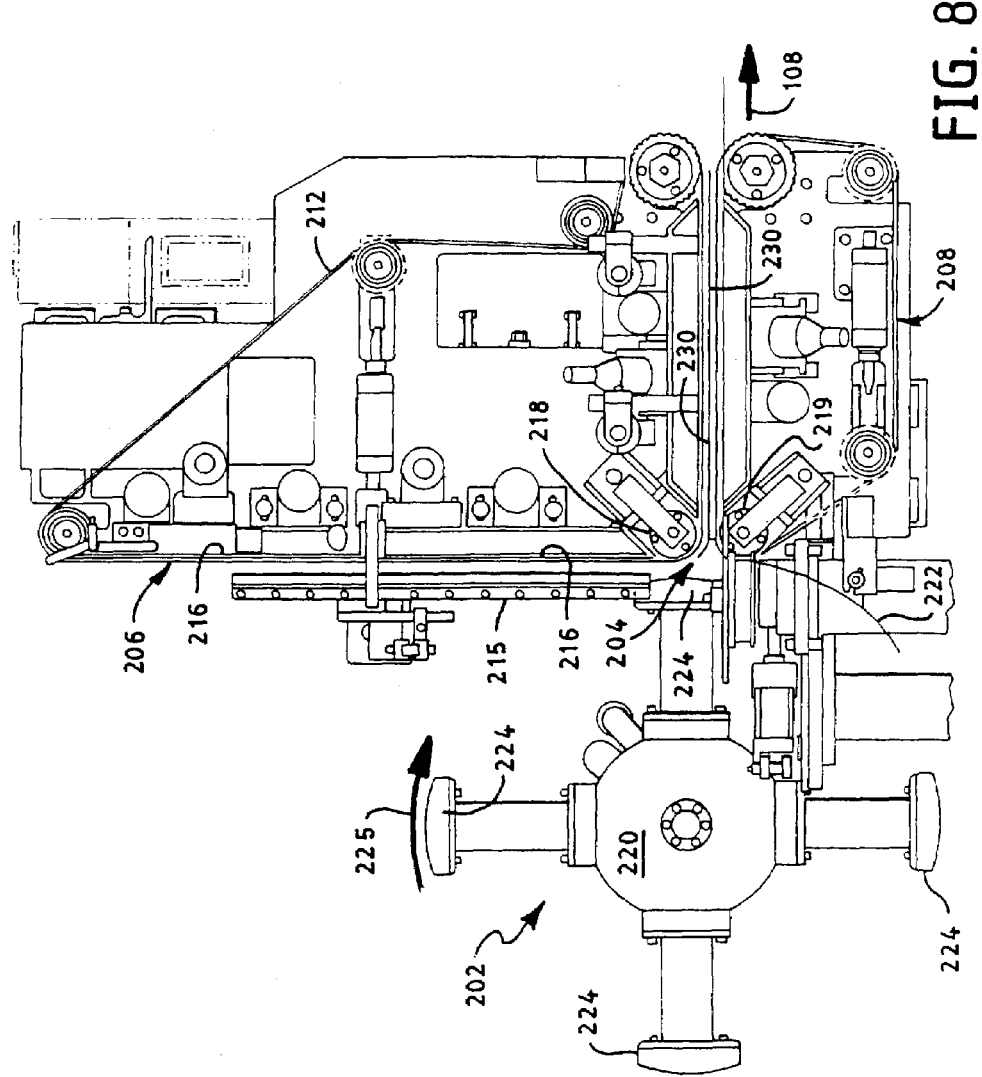
FIG. 8 illustrates an enlarged side view of the folding section shown in FIG. 2.
Figure 9:
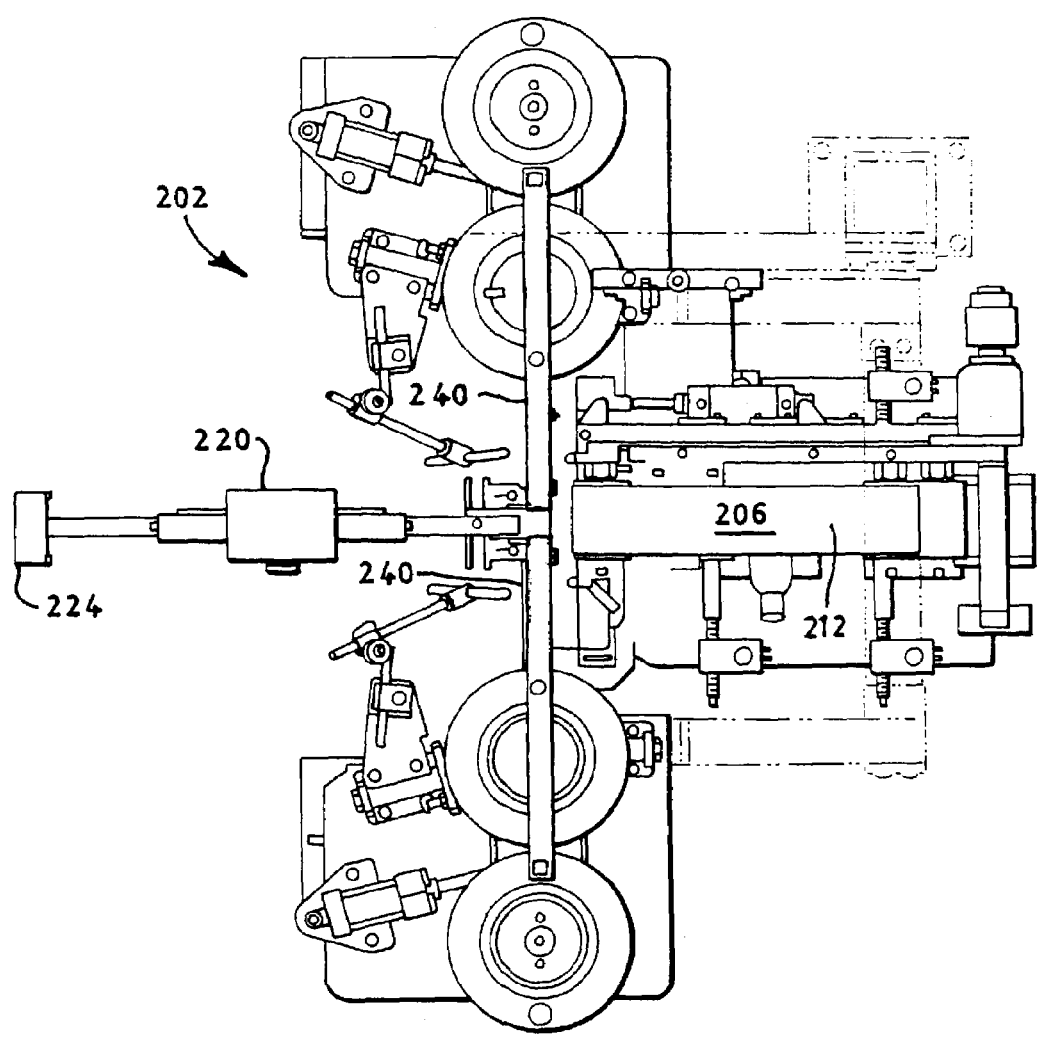
FIG. 9 illustrates a top view of a portion of the folding section shown in FIG. 2.

A variety of folding mechanisms 202 can be used, such as blade folders, linear folders, book folders, tucker blades or the like. The specific type selected for a given application may depend upon the type of garment being manufactured and the type of fastening mechanism used to secure the garment in a pant configuration. An embodiment of a blade folding mechanism 202 adapted for use with garments incorporating refastenable fastening components 82–85 is illustrated in FIGS. 2, 8 and 9. The illustrated folding mechanism 202 controls the side panels 34 and 134 during folding so that the refastenable fastening components 82–85 are unlikely to engage one another or engage another material during the folding operation. Other arrangements for maintaining separation of the side panels and fastening components during folding are disclosed in U.S. Pat. No. 6,514,187, issued Feb. 4, 2003 to J. D. Coenen et al. and titled "Folding And Manufacture Of Pants," which is incorporated herein by reference.

The illustrated blade folding mechanism 202 comprises a plurality of rotating folding or tucker blades which are configured to contact the training pant 102 along the fold line. Rotation of the folding blades can force the training pant 102 into a nip 204 between two rotating folding conveyors 206 and 208 causing the training pants to fold about the fold line. The folding conveyors 206 and 208 can form part of a transport system for moving the folded training pants 102 in the machine direction 108. The folded training pants 102 are illustrated as being transported in the machine direction 108 with the crotch region 26 leading the waist regions 22 and 24. Alternatively, the process and apparatus could be modified so that the waist regions lead the crotch region (not shown).

With reference to FIGS. 2, 8 and 9, the series of unfolded, discrete training pants 102 can be transferred from the vacuum anvil roll 188 of the cutter 186 to the upper folding conveyor 206. The training pants 102 can be held by vacuum on the upper folding conveyor 206 and transported toward the nip 204 formed between the folding conveyors 206 and 208. While being transported toward the nip 204, the side panels 34 and 134 can be smoothed out or straightened if desired by various means including fluid stabilizing devices. For example, air knives 215 (FIG. 8), air bars, air nozzles or the like can be mounted in proximity to the upper folding conveyor to provide a stream of fluid directed toward the side panels to stabilize and/or straighten the side panels. The air knives 215 can blow the side panels 34 and 134 toward or against skid plates 216 positioned transversely outward from the upper folding conveyor belt 212. Alternatively, or in addition thereto, the upper folding conveyor 206 can incorporate fluid stabilizing devices consisting of fluid manifolds operatively connected to a high pressure fluid source to fluidly shake the side panels. The fluid stabilizing devices desirably prevent folding of the side panels 34 and 134 as the training pant 102 moves along the upper folding conveyor 206. Sensing devices can also be employed at this point to detect products that have folded side panels or that are misaligned relative to the machine center line.

The product folding nip 204 can be formed between a timed vacuum nose roll 218 of the upper folding conveyor 206 and a timed vacuum nose roll 219 of the lower folding conveyor 208 (FIGS. 2 and 8). As the leading edge of a pant 102 is introduced onto the upper nose roll 218, compressed air can be introduced inside the nose roll to negate vacuum draw of the nose roll. This allows the leading edge of the pant to pass by the nose roll 218 without getting sucked into the nip 204. Alternatively of course, the vacuum source can be temporarily disconnected from the nose roll 218. Any suitable control system can be used to repeatedly activate and deactivate vacuum operation of the nose rolls 218 and 219. In particular embodiments, rotary valves can be employed to cycle vacuum to the nose rolls 218 and 219.

A product control drum 220 can guide the leading half of the training pant 102 onto a curved transfer plate 222 (FIGS. 2 and 8). The product control drum 220 can comprise a plurality of vacuum pucks 224 which rotate in the direction of arrow 225. The illustrated product control drum 220 includes four vacuum pucks 224 to guide four training pants 102 per revolution. Rotation of the product control drum 220 can be timed so that a vacuum puck 224 grabs the leading half of a training pant 102 and transfers the leading edge onto the curved transfer plate 222. The absorbent chassis 32 and/or side panels 134 of the leading half can be carried on a vacuum puck 224 past the nose roll 219 of the lower folding conveyor 208. Compressed air can be introduced inside this lower nose roll 219 at this point to negate vacuum draw and permit the entire leading edge and side panels 134 to transfer onto the curved transfer plate 222. Alternatively of course, the vacuum source can be temporarily disconnected from the nose roll 219.

With reference to FIG. 9, the folding mechanism 202 can comprise a pair of opposed tucker blades 240 that move in an orbital manner to pass through the vertical path of the training pant 102. The tucker blades 240 can contact the crotch region 26 of the pant 102 and insert the crotch region into the folding nip 204. As this happens, the leading half of the pant 102 reverses direction over the curved transfer plate 222 and is pulled into the nip 204. The vacuum puck 224 can cease drawing vacuum at this point to release the leading half. Correspondingly, the trailing half of the pant 102 is pulled around the upper nose roll 218. Thus, both halves of the training pant 102 can change from motion in a generally vertical plane to motion between the folding conveyors 206 and 208 in a generally horizontal plane.

Figure 10:
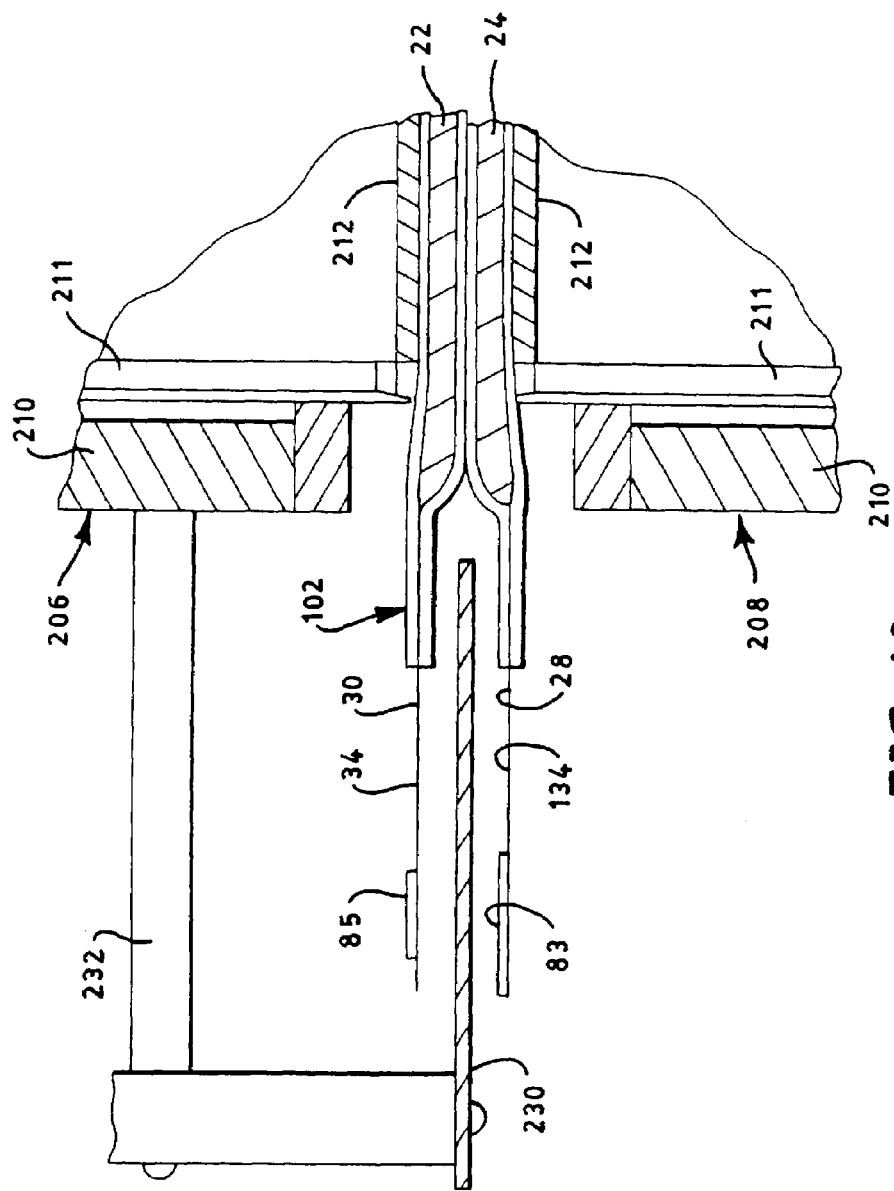
FIG. 10 illustrates an enlarged section view of a portion of a training pant at a position within the folding section shown in FIGS. 2, 8 and 9.

The illustrated folding mechanism 202 can maintain separation between the front and back side panels 34 and 134. As the pant 102 enters the folding nip 204, compressed air can be shut off to the upper nose roll 218 so that the side panels 34 of the trailing half are drawn by vacuum to the upper nose roll. The trailing side panels 34 are thus drawn to the upper nose roll 218 and follow its rotation around the roll and over side panel separation plates 230 (FIGS. 2, 8 and 10). Similarly, as the leading half of the pant 102 is pulled into the folding nip 204, compressed air can be shut off to the lower nose roll 219 so that the side panels 134 of the leading half are drawn by vacuum to the lower nose roll. The leading side panels 134 are thus drawn to the lower nose roll 219 and follow its rotation around the roll and beneath the side panel separation plates 230.

FIG. 10 illustrates a portion of a partially assembled training pant 102 positioned between the upper and lower folding conveyors 206 and 208 at a location downstream of the nose rolls 218 and 219. At this point, the training pant 102 has been folded in half and is being transported in the machine direction 108 by the conveyors 206 and 208. The illustrated folding mechanism 202 can thus maintain the front side panels 34 separated from the back side panels 134 during folding.

Each folding conveyor 206 and 208 as illustrated in greater detail in FIG. 10 can comprise a frame structure 210, a plurality of rotatable pulleys 211 associated with the frame structure, and a continuous belt 212 carried on the pulleys. A drive system and conveyor shaft (not shown) can be used to rotatively drive one or more of the pulleys. The folding conveyors 206 and 208 can comprise vacuum conveyors as are well known in the art, in which case the continuous belt can be formed of a fluid permeable material. The folding conveyors desirably transport the training pants 102 with the longitudinal center line of the training pants traveling on the longitudinal center line of the conveyors. As depicted, the front and back side panels 34 and 134 can project laterally outward from the frame structure 210, outstretched in the cross-machine direction.

While traveling on the folding conveyors 206 and 208, the side panels 34 and 134 can be smoothed out or straightened if desired by various means including fluid stabilizing devices (not shown in FIG. 10). Suitable fluid stabilizing devices can comprise air knives, air bars, air nozzles, vacuum devices or the like to provide a stream of fluid directed toward the side panels. The fluid stabilizing devices can be incorporated within either or both of the folding conveyors 206 and 208 or can comprise separate devices positioned in proximity to the conveyors.

As a result of the illustrated folding mechanism 202, the front waist region 22 and front side panels 34 of the partially assembled training pant 102 are disposed above the back waist region 24 and back side panels 134. The first fastening component 83 is disposed on the inner surface 28 of the back side panel 134 and the second fastening component 85 is disposed on the outer surface 30 of the front side panel 34. The separation plate 230 can extend in the machine direction 108 to maintain separation between the front and back side panels 34 and 134. The separation plate 230 can comprise a low friction material or coating, such as: stainless steel; teflon; aluminum; ultra-high molecular weight polyethylene (UHMW-PE); polyoxymethylene (acetals), for instance a homopolymer available from E. I. Du Pont de Nemours and Company, Wilmington, Del. USA under the tradename DELRIN; or the like. In particular embodiments, the separation plate 230 can comprise a thin layer of teflon, UHMW-PE, DELRIN or the like glued to a plate formed of steel, aluminum or the like. The separation plate can be mounted using suitable support members 232 (FIG. 10) to either the folding conveyors 206 or 208 or other suitable frame structures (not shown).

The terms "upper" and "lower" are provided for ease of understanding, and it should be recognized that the spatial arrangement of the elements being described could be inverted or arranged in another manner. Use of the terms "vertical" and "horizontal" and variations thereof have their usual meaning, however, the present invention contemplates that vertical surfaces can be "generally vertically" disposed if desired and would thus be oriented between the true vertical position and about a 45 degree position relative to the true vertical position. The same interpretation for "generally horizontally" disposed means an orientation between the true horizontal and about a 45 degree position relative thereto.

From the folding station 200, the continuous stream of discrete, partially assembled and folded training pants 102 enter a seaming section 250, an embodiment of which is shown in FIG. 3. The seaming section 250 can encompass processes and apparatus for controlling the unattached side panels 34 and 134, guiding the side panels into an overlapping orientation to form a lap seam, and bonding the side panels together.

In general, the processes and apparatus can bend or fold the front or back side panels 34 or 134 using an interior folding mechanism 251. After one pair of side panels is oriented in this manner, an exterior folding mechanism 252 can fold the other pair of side panels so that they are positioned transversely outward from the first pair of side panels (see FIG. 18). A fastener engagement mechanism 253 can then cause the side panels to be brought into contact with one another and/or bonded together. In the embodiment shown in FIG. 4, the side panels are refastenably bonded together using mating mechanical fastening components 82–85, although other refastenable or permanent bonding arrangements can also be used. The seaming section 250 can thus convert the partially assembled and folded training pants 102 into prefastened training pants 20 each having a waist opening 50 and a pair of leg openings 52 (FIG. 4). The illustrated seaming section 250 could of course be inverted so that the lower side panel is first folded upward to form the inner side panel of the lap seam (not shown). From the seaming section 250, the training pants 20 can be processed through various finishing stations 254, for operations such as side panel tucking, packaging, or the like.

The partially assembled training pants 102 can be transported in the machine direction 108 through the seaming section 250 by a transport system, such as conveyors or other suitable means. In the illustrated embodiment, the training pants 102 are transferred from the upper and lower folding conveyors 206 and 208 (FIGS. 2 and 8–10) to upper and lower alignment conveyors 256 and 258 (FIGS. 3 and 13–18). The upper alignment conveyor 256 can comprise a frame structure 260, a plurality of rotatable pulleys 261 (FIG. 3) associated with the frame structure, and a continuous belt 262 carried on the pulleys. Similarly, the lower alignment conveyor 258 can comprise a frame structure 270, a plurality of rotatable pulleys 271 (FIG. 3) associated with the frame structure, and a continuous belt 272 carried on the pulleys. A drive system and conveyor shafts (not shown) can be used to rotatively drive one or more of the pulleys. The alignment conveyors 256 and 258 can comprise any suitable conveyor mechanisms such as vacuum conveyors or non-vacuum conveyors. Suitable conveyor mechanism are available from various commercial vendors. Alternatively, the transport system can comprise any means to transport the folded products.

Figure 11:
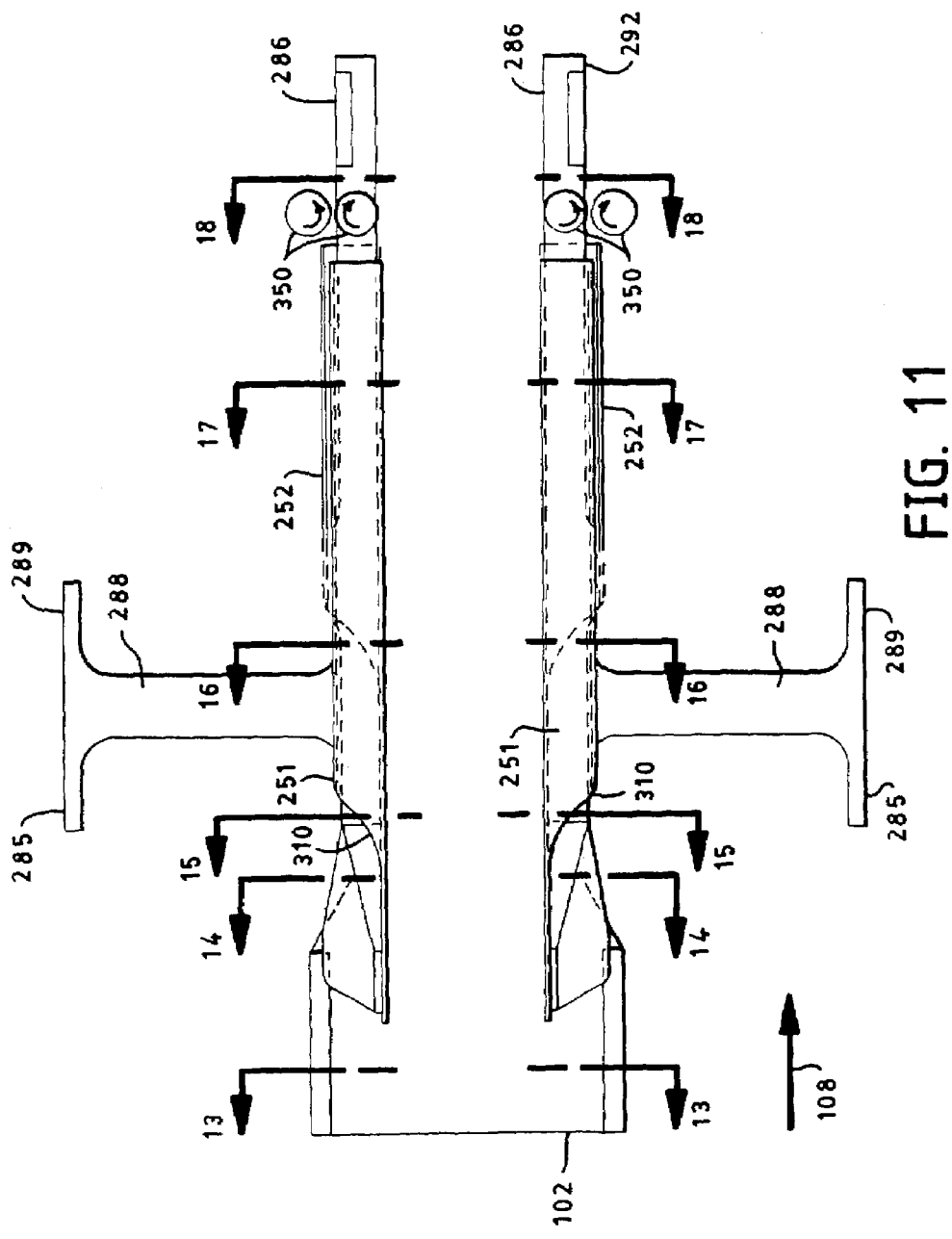
FIG. 11 schematically illustrates a top view of a side panel seam forming apparatus shown in FIG. 3.
Figure 12:
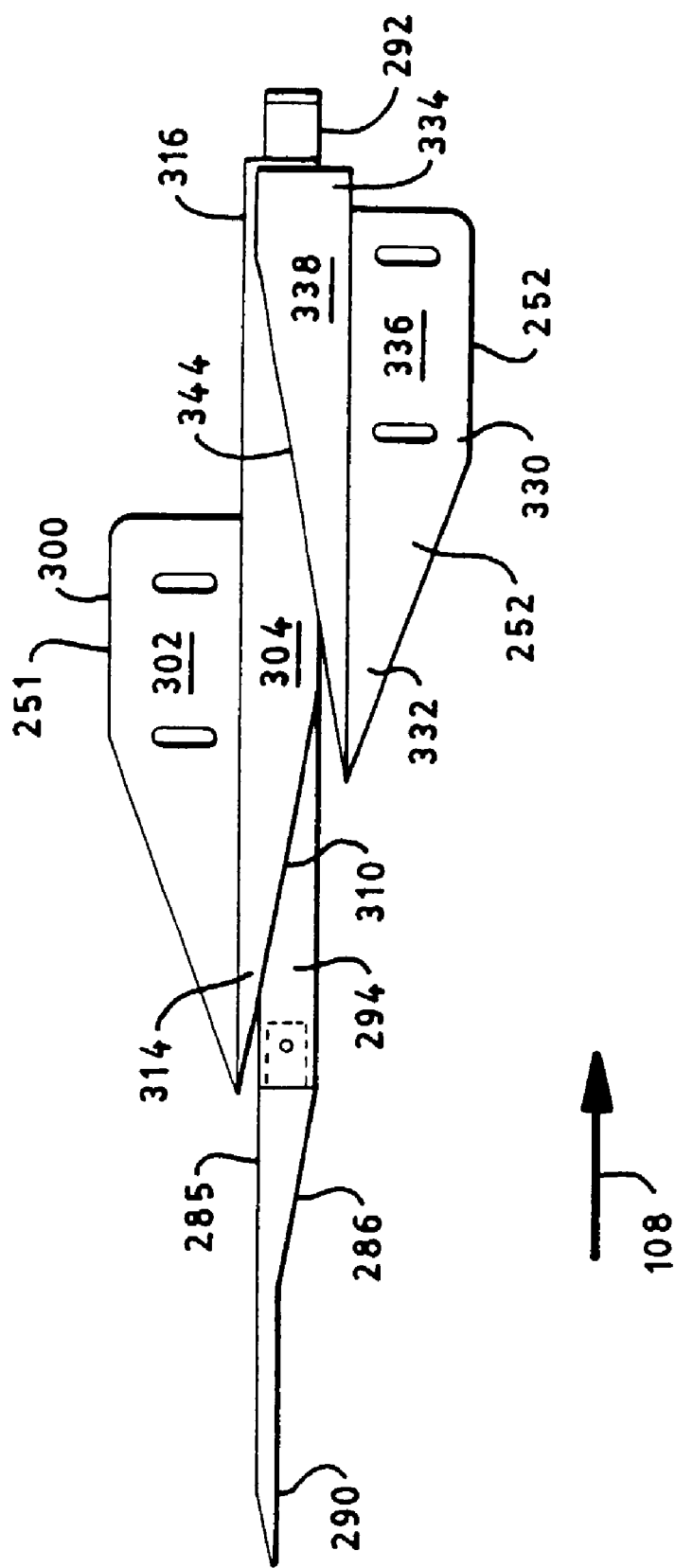
FIG. 12 illustrates an enlarged side view of a mandrel and interior and exterior folding mechanisms of the side panel seam forming apparatus shown in FIG. 11.

Formation of the side panel lap seam will be described in greater detail with reference to FIGS. 11–18. FIG. 11 schematically illustrates a top view of a side panel seam forming apparatus including the interior and exterior folding mechanisms 251 and 252 shown in FIG. 3, although not showing the alignment conveyors 256 and 258. FIG. 12 illustrates an enlarged side view of the interior and exterior folding mechanisms 251 and 252. The interior folding mechanism 251 can position one of the side panels 34 or 134 on each side of the training pant 102 to form the interior side panel of the lap seam. The exterior folding mechanism 252 can position the other of the side panels 34 or 134 on each side of the training pant 102 to form the exterior side panel of the lap seam. FIGS. 13–18 illustrate enlarged section views of a portion of a training pant within the side panel seam forming apparatus at a series of positions represented by section lines 13—13 through 18—18 in FIG. 11. In the illustrated embodiment, the front side panels 34 including the second fastening components 84 and 85 form the interior side panels of the lap seam, and the back side panels 134 including the first fastening components 82 and 35, 83 form the exterior side panels of the lap seam. Alternatively, of course, the front side panels could form the exterior side panels of the lap seam and/or could include the first fastening components. The description will focus on the formation of a lap seam and bonding the side panels 34 and 134 together on one side of the training pant 102, although it should be recognized that a lap seam can be formed on the other side of the training pant in a similar manner. The refastenable seams 88 can be formed simultaneously or sequentially on the right and left sides of the pant 102. The components of the folding mechanisms 251 and 252 can comprise rigid structures, if desired, which can provide folding of the side panels as they are transported in the machine direction without requiring more complicated and potentially less dependable systems utilizing moving components.

Figure 13:
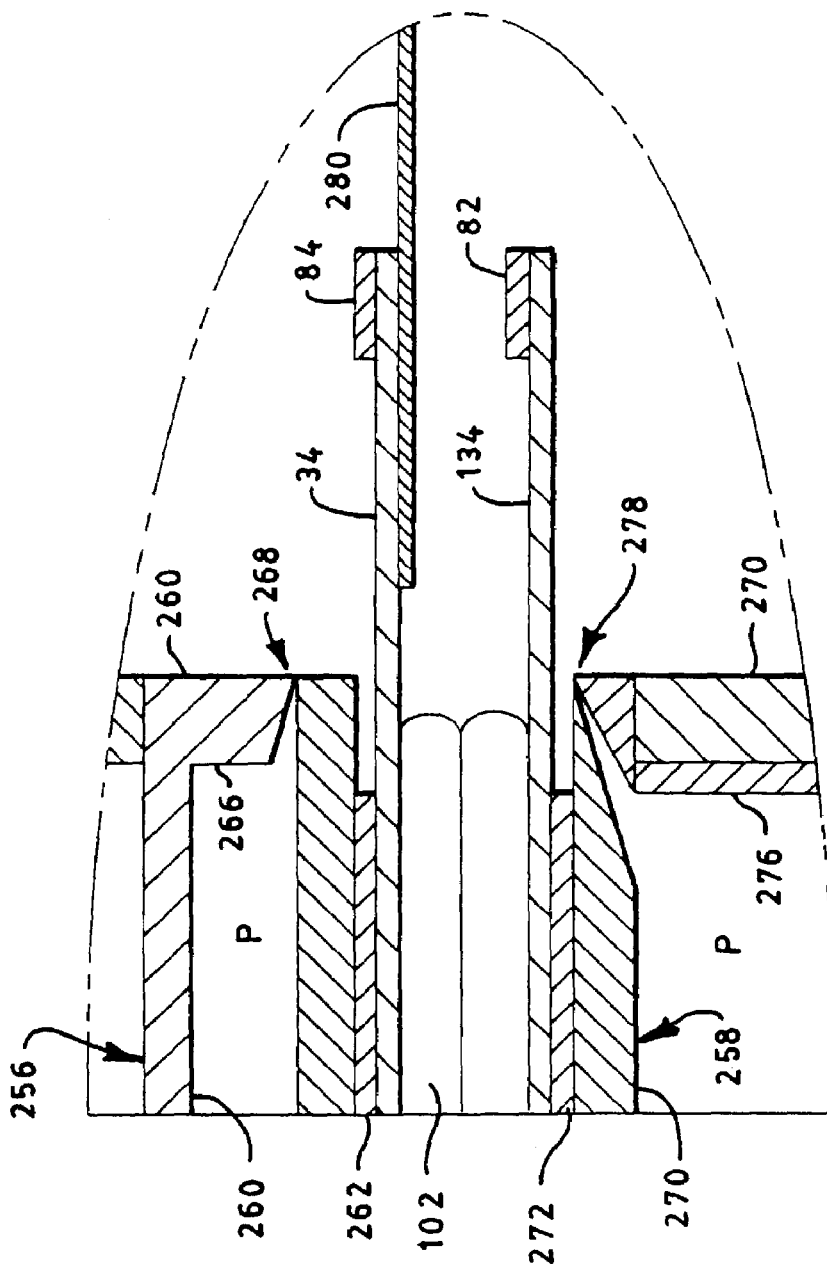
FIGS. 13–18 illustrate enlarged section views of a portion of a training pant within the side panel seam forming apparatus shown in FIG. 11 at a series of positions represented by lines 13—13 through 18—18 in FIG. 11.

FIG. 13 illustrates the training pant 102 positioned between the upper and lower alignment conveyors 256 and 258 at a location downstream of the location illustrated in FIG. 10. As illustrated, the front side panels 34 can be disposed on or in close proximity to a skid plate 280. The skid plate can support the upper side panels 34, maintain separation of the side panels 34 and 134, and establish greater separation for subsequent folding operations. The front side panels 34 can be transitioned onto the skid plate 280 from the separation plate 230 (FIG. 10) by any suitable means. Alternatively, the skid plate 280 and the separation plate 230 can be integrally formed. The skid plate 280 can be rigidly mounted on the alignment conveyors 256 or 258 or another suitable structure. The skid plate 280 can be formed of the same materials as the separation plate 230.

As further illustrated in FIG. 13, one or both of the side panels 34 and 134 can be smoothed out or straightened if desired by various means including fluid stabilizing devices. As shown in FIG. 13, for example, the frame structures 260 and 270 of the alignment conveyors 256 and 258 can define internal chambers 266 and 276, respectively, that can be connected to a source of pressurized fluid (not shown). The frame structures 260 and 270 can further define fluid manifolds each comprising a plurality of nozzles 268 and 278, respectively. The pressurized fluid can be expelled through the nozzles 268 and 278 in a direction transversely outward from the conveyor center line and toward the side panels 34 and 134 to fluidly shake the side panels.

The fluid stabilizing devices can alternatively comprise air knives, air bars, air nozzles, vacuum devices or the like to provide a stream of fluid to stabilize and/or straighten any of the side panels. Suitable mechanisms for smoothing and straightening the side panels 34 and 134 are disclosed in U.S. Pat. No. 5,046,272 issued Sep. 10, 1991 to Vogt et al., which is incorporated herein by reference. The terms "air" and "fluid" are used interchangeably herein to refer to any gaseous substance, for example, air at ambient temperature. Where the specific application permits, the term "fluid" also includes any liquid medium.

The side panel seam forming apparatus can include cantilevered folding horns or mandrels 285 (FIGS. 11, 12 and 14–18). Each mandrel 285 as illustrated can comprise a tubular body 286, a support arm 288 (FIGS. 11 and 16–18) and a mounting flange 289 (FIG. 11), which portions can be integrally formed or separate elements bonded together. The tubular body 286 can be aligned generally parallel with the machine direction 108 and be positioned in the same plane as the training pant 102. The tubular body 286 can define an upstream end 290, an opposite downstream end 292 and a peripheral surface 294. The tubular body 286 can further define an internal chamber 296 (FIGS. 16 and 17) that extends over at least a portion of the length of the tubular body.

The internal chamber 296 can be operatively connected to a source of vacuum by any suitable means, for example, ports (not shown) extending through the support arm 288. The tubular body 286 can further define an aperture 298 (FIGS. 16 and 17) that connects the internal chamber 296 with the space surrounding the tubular body. The aperture 298 can comprise, for example, a slot having a width of approximately 3.2 millimeters and any suitable length generally parallel to the machine direction 108.

The size of the tubular body 286 will depend to some extent on the size of the side panels and the fastening components of the garment. In one particular embodiment, for instance, the tubular body 286 can have length dimension of approximately 0.62 meters, a maximum outside diameter of approximately 4.4 centimeters, and a wall thickness of approximately 0.6 centimeters. The tubular body 286 can desirably be formed of a low friction material to allow the side panels to slide over the peripheral surface 294. In particular embodiments, the tubular body 286 can comprise structural tubing of low carbon steel, polycarbonate material, or the like. The mounting flange 289 can be connected to any suitable support structure (not shown).

The illustrated interior folding mechanism 251 is in the form of interior forming shoulders 300 (FIGS. 12 and 15–18). The forming shoulders 300 are referred to as "interior" because they can be employed as in the illustrated embodiment to position one pair of the side panels of the training pant 102 to form the "interior" panels of the lap seams. Each illustrated interior forming shoulder 300 comprises a mounting flange 302 and a forming surface 304 projecting transversely outward from the mounting flange. The mounting flange can be bonded to the upper alignment conveyor 256 by fasteners, welding, or other suitable means. The forming surface 304 defines an interior surface 306 which is disposed toward the front side panel 34 and an opposite exterior surface 308 (FIGS. 15–18). The forming surface 304 further defines a distal edge 310 which is located remote from the mounting flange 302. The interior forming shoulder 300 has an upstream end 314 and an opposite downstream end 316, and as shown in FIGS. 11 and 12, the distal edge 310 can be tapered near the upstream end.

Figure 16:
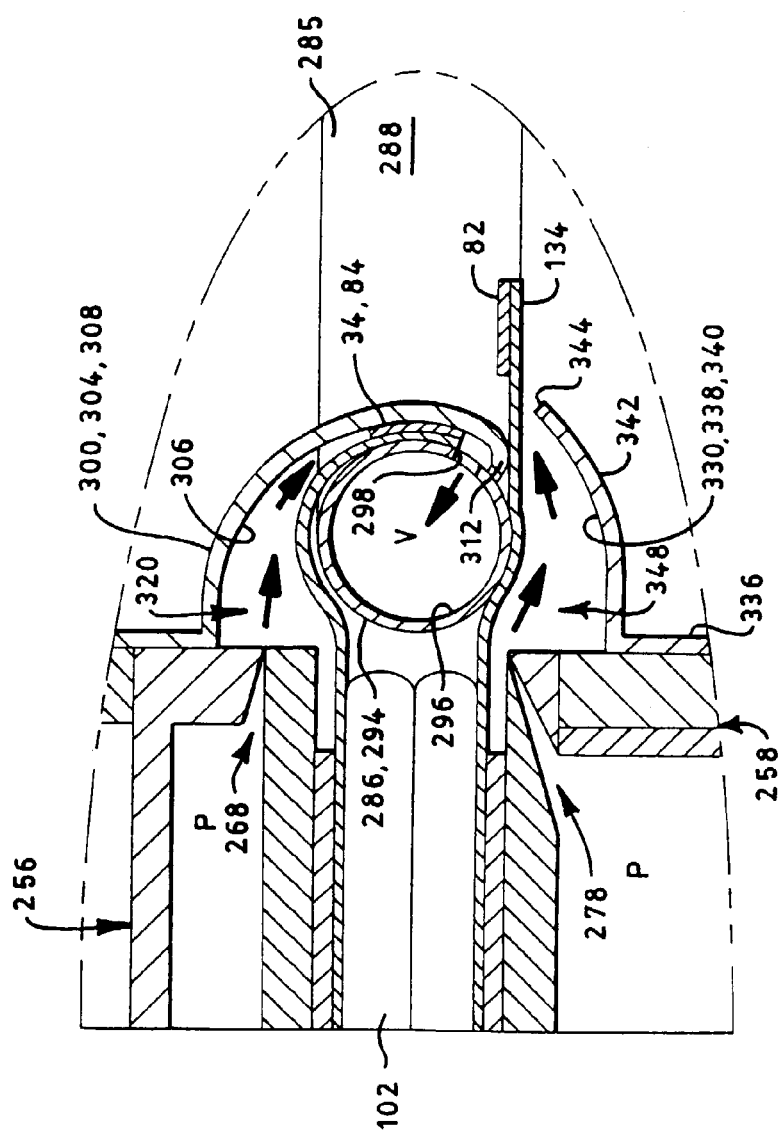
Figure 17:
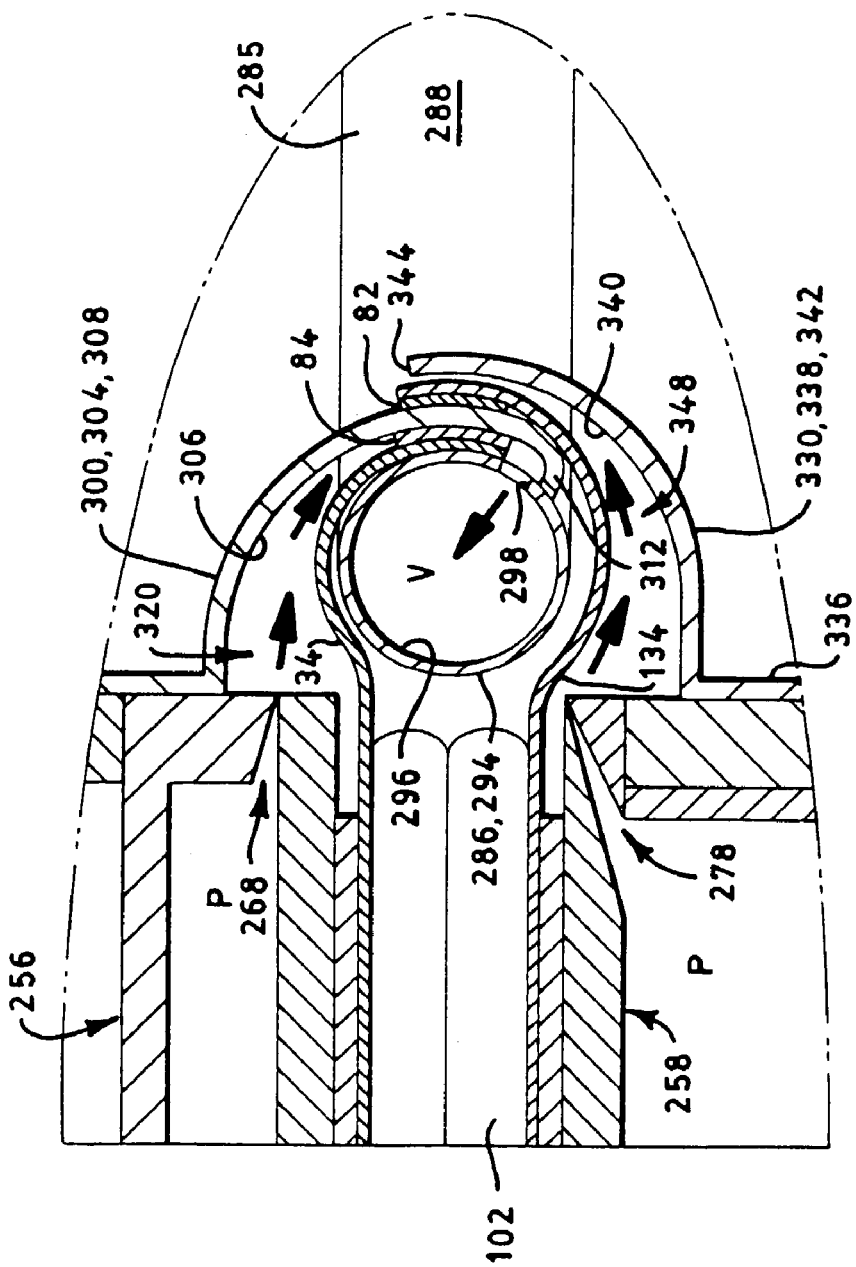
Figure 18:
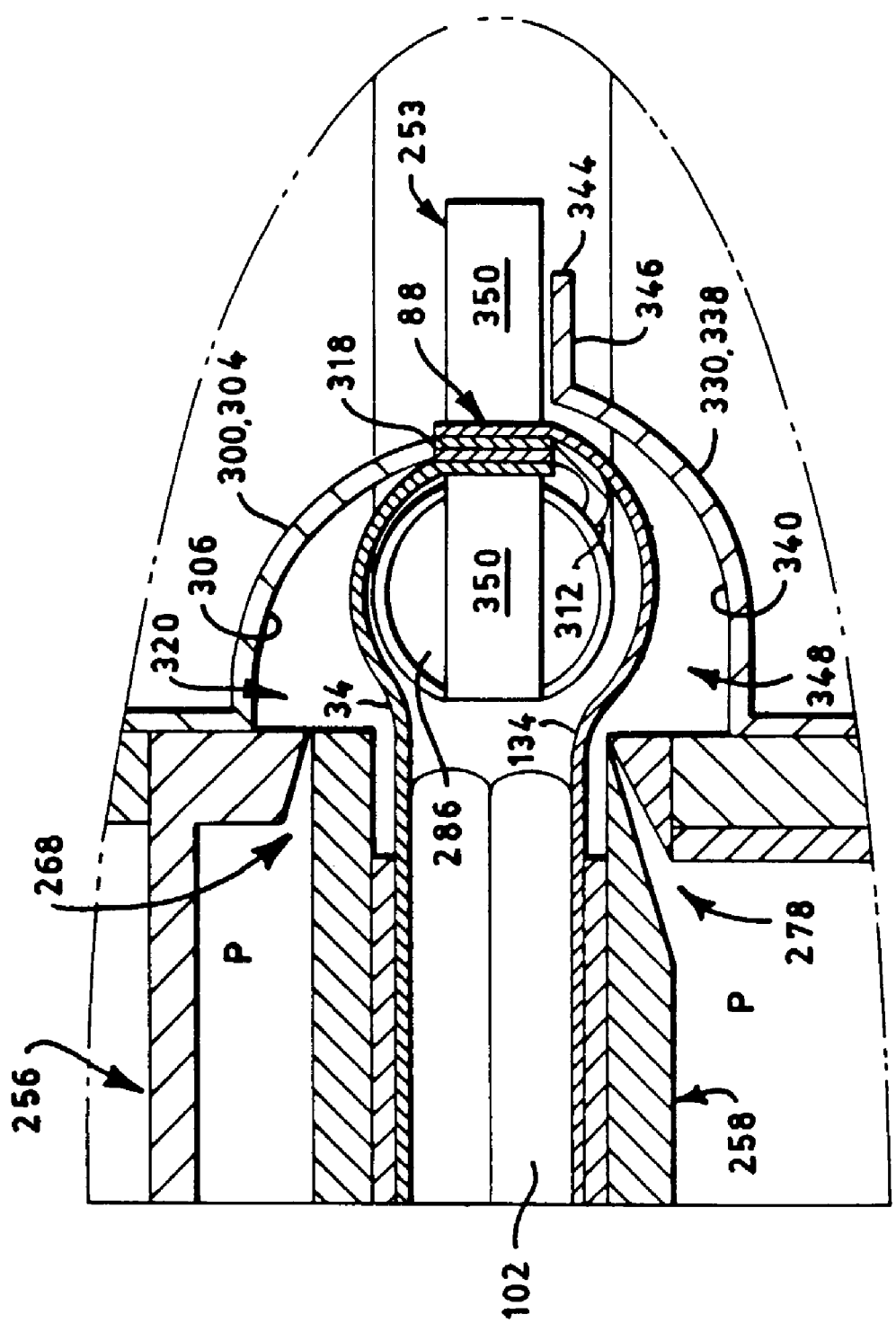

With reference to FIGS. 16–18, the forming surface 304 can define a head portion 312 adjacent the distal edge. The interior forming shoulder 300 can be shaped such that the head portion 312 is closer to the curved peripheral surface 294 at downstream machine direction positions. In particular embodiments, the head portion 312 can reside in friction contact with or be bonded to the mandrel tubular body 286, either over its full machine direction length or only at downstream positions. In one particular embodiment, the peripheral surface 294 of the mandrel tubular body 286 defines a recessed portion and the head portion 312 of the interior forming shoulder 300 is seated in the recessed portion (not shown). The interior forming shoulders 300 can comprise any material that will permit folding of the front side panels 34, and desirably comprise a low friction material such as stainless steel, aluminum, sheet steel which is buffed or coated to provide low resistance, or the like.

The mandrel 285 and the interior forming shoulder 300 can operate together to guide the front side panel 34 into position for forming a lap seam. At the machine direction position illustrated in FIG. 14, the upstream end 290 (FIG. 12) of the tubular body 286 can be introduced between the front and back side panels 34 and 134. The upstream end 290 can be introduced adjacent to or in contact with the skid plate 280. Fluid expelled from the nozzles 268 can function at this point to control and straighten the upper side panel 34. From the position illustrated in FIG. 14 to the downstream position illustrated in FIG. 15, the front side panel 34 can be transferred to the tubular body 286.

Additionally, the diameter of the tubular body 286 can increase. The interior forming shoulder 300 can be introduced at the location illustrated in FIG. 15, and the tubular body 286 and the interior forming shoulder 300 can define therebetween an inner passage 320. The interior forming shoulder 300 can be mounted to the upper alignment conveyor 256 with the fluid nozzles 268 disposed between the front side panels 34 and the interior forming shoulder mounting flange 302. Fluid expelled from the nozzles 268 into the inner passage 320 as depicted by the arrows tends to force the front side panels 34 around the cylindrical contour of the tubular body 286, and can reduce drag against the forming surface 304. The forming surface 304 can be curved toward the mandrel 285 to further direct fluid to force the side panels against the mandrel 285.

By the machine direction position illustrated in FIG. 16, the interior forming shoulder 300 has reached its maximum width and the head portion 312 can be disposed in contact with the peripheral surface 294 of the tubular body 286. The illustrated internal forming shoulder 300 increasingly curves or wraps around the mandrel 285 at downstream machine direction positions. As illustrated, the head portion 312 desirably contacts the peripheral surface 294 at a position beyond the location of the tubular body aperture 298. In this way, the mandrel internal chamber 296 can be in fluid communication with the inner passage 320.

When the mandrel internal chamber 296 is connected to a vacuum source, the induced air flow through the aperture 298 as depicted by the arrows can pull the front side panel 34 toward the tubular body 286 and conform the side panel to the peripheral surface 294. In one embodiment, the internal chamber 296 and aperture 298 can be located at a machine direction location within the tubular body 286 so that vacuum begins when the forming surface 304 is at its maximum width and is seated on the mandrel 285.

The side panel seam forming apparatus can be operated with pressurized fluid from the nozzles 268 and/or with vacuum drawn within the tubular body 286, or with neither. When vacuum is used, the level of vacuum within the internal chamber 296 can vary depending upon the application, for example, from 0 to about 8 inches of water or greater below atmospheric pressure, and more particularly from about 2 to about 8 inches of water or greater below atmospheric pressure. The vacuum can encourage air flow along the curved interior forming surface 306. The pressurized fluid from the nozzles 268 (when used) can be exhausted to atmosphere, however, exhausting to the internal chamber 296 prevents the pressurized fluid from disrupting the position of the back side panels 134.

The aperture 298 can be located at an angular position on the tubular body 286 so that it is beyond the distal edge of the front side panel 34 when the side panel is folded around the peripheral surface 294. In the illustrated embodiment, the aperture 298 is located approximately 45 degrees below horizontal with respect to the tubular body 286. The angular location for any particular application will depend in part on the size, shape and position of the tubular body and the desired amount of overlap of the side panels in the lap seam. The size of the tubular body 286 can be selected so that the front side panels 34 are supported outward of the upper alignment conveyor 256 over substantially the entire side panel width. In one particular embodiment, for example, the tubular body 286 can be positioned transversely outward from the upper alignment conveyor 256 by a distance of about 3 centimeters.

The interior forming shoulder 300 and the mandrel 285 can cooperatively guide the front side panels 34 into position to form a lap seam. The side panels can be wrapped over the tubular body 286 squarely so that the distal edges of the side panels and/or the second fastening components 84 and 85 are generally horizontal. At the location of the second fastening components 84 and 85, the gap between the forming surface 304 and the mandrel peripheral surface 294 can be selected to permit complete movement of the fastening components around the tubular body 286 without preventing proper folding of the back side panels 134. For particular embodiments, the gap at the location of the second fastening components 84 and 85 can be from about 2 to about 40 millimeters, for example, about 30 millimeters.

The exterior folding mechanism 252 can comprise any suitable mechanism adapted to guide the back side panels 134 into overlapping position relative to the front side panels 34 to form a lap seam. In the illustrated embodiment, the exterior folding mechanism 252 comprises exterior forming shoulders 330, which can be formed of the same materials as the interior forming shoulders 300. Each exterior forming shoulder 330 has an upstream end 332 and an opposite downstream end 334 (FIG. 12), and can comprise a mounting flange 336 (FIGS. 12 and 14) attached to the lower alignment conveyor 258 and a forming surface 338 extending transversely outward from the mounting flange. The forming surface 338 defines an interior surface 340 disposed toward the back side panels 34 and an opposite exterior surface 342. The forming surface 338 also defines a distal edge 344 remote from the mounting flange 336 and extending between the upstream and downstream ends 332 and 334. At the machine direction location illustrated in FIG. 18, the forming surface 338 can form a flange 346 adjacent the distal edge 344. An outer passage 348 can be formed between the forming surface 338 and the tubular body 286, and the fluid nozzles 278 can blast fluid into the outer passage as depicted by the arrows in FIGS. 15–18.

Figure 14:
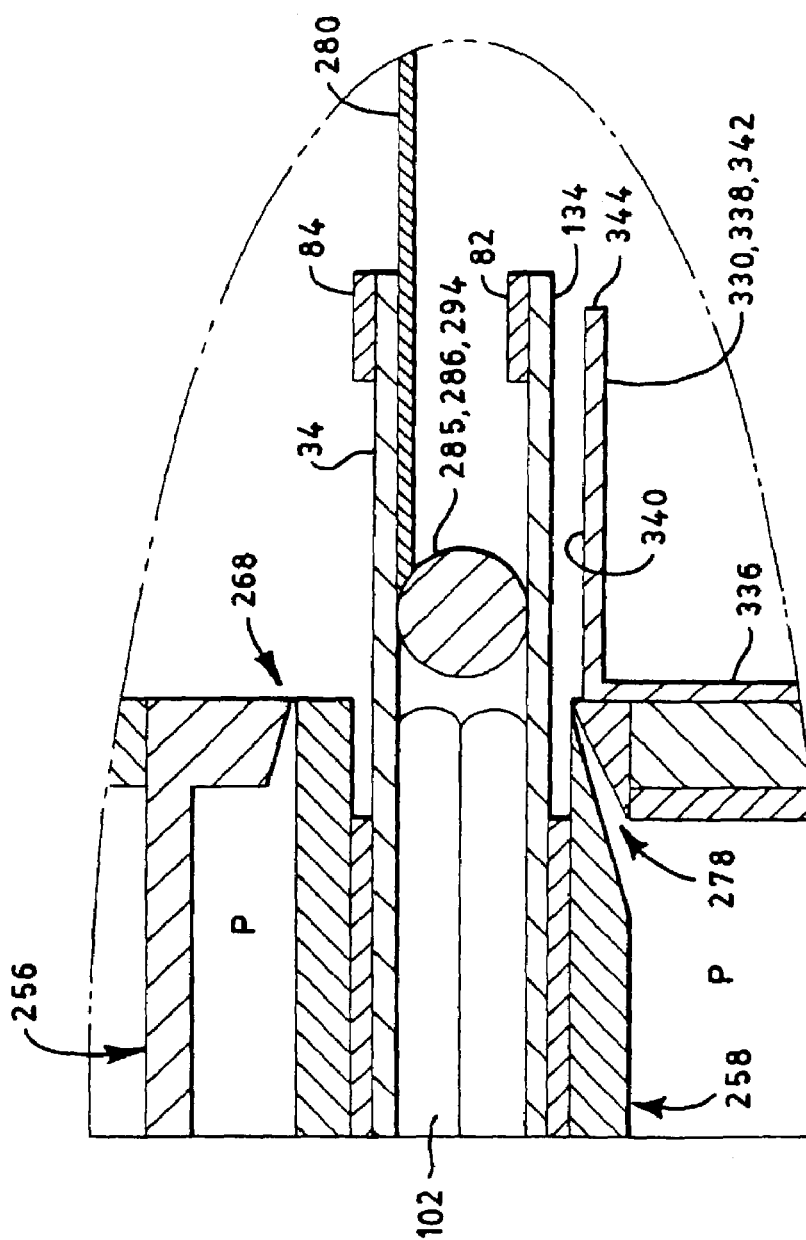
Figure 15:
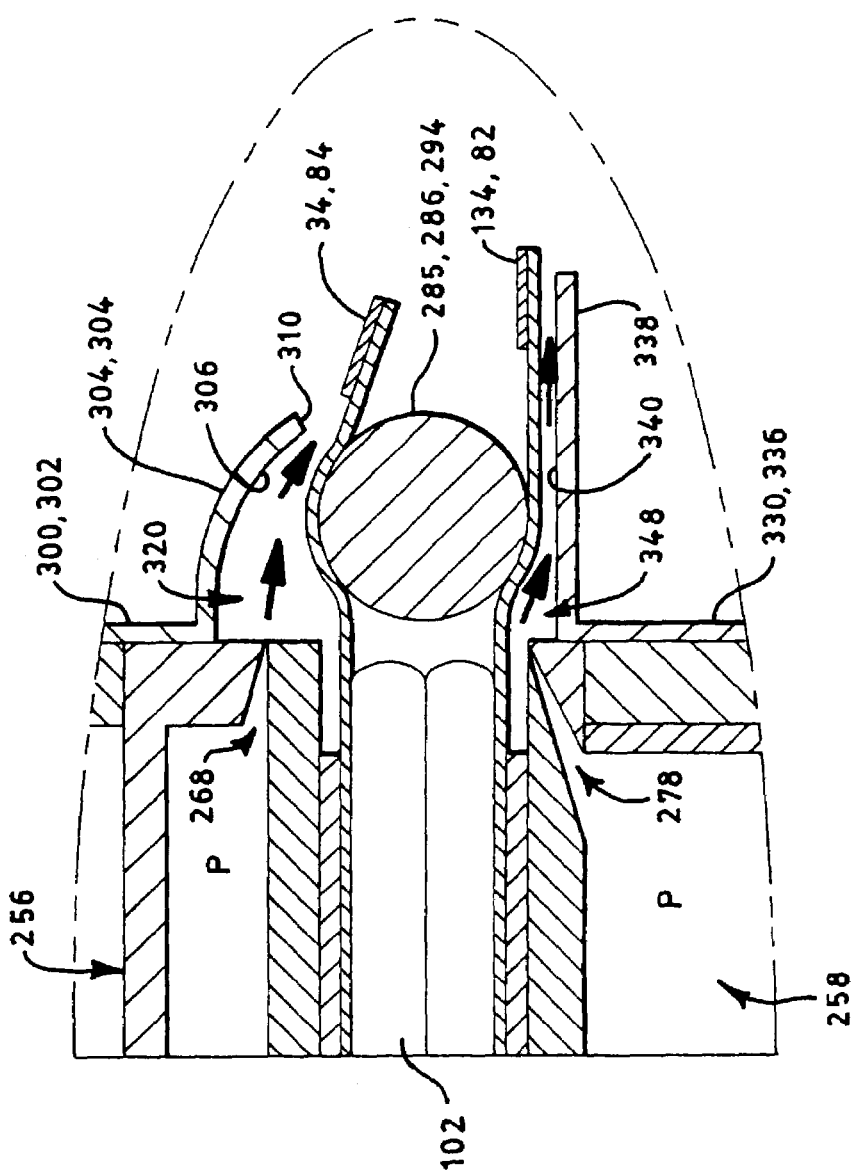

The forming surface 338 of the exterior forming shoulder 330 can be generally flat at the machine direction position illustrated in FIGS. 14 and 15. Fluid from the nozzles 278 can function to control and straighten the back side panels 134. At downstream locations such as those illustrated in FIGS. 16 and 17, the forming surface 338 can have an inwardly curved inner surface 340 that directs the air flow and thus the back side panel 134 around and over the mandrel peripheral surface 294 and the exterior surface 308 of the interior forming shoulder 300. The forming surface 338 and adjacent portions of the mandrel peripheral surface 294 can be curved in the same direction, which is opposite that of forming surface 304. The air stream from the nozzles 278 can be exhausted to atmosphere, particularly because that flow path does not disrupt the position of the front side panels 34. The exterior folding mechanism 252 can employ forced air and/or vacuum or neither to shape the back side panels 134 to the shape of the interior surface 340.

As depicted in FIG. 17, the exterior forming shoulder 330 can in part be positioned transversely outward from and overlap the interior forming shoulder 300. The peripheral portion of the exterior forming shoulder 330 near the distal edge 344 can be positioned in close proximity to the peripheral portion of the interior forming shoulder 300, particularly so that the fastening components 82–85 are positioned in close proximity to one another. The size and positioning of the tubular body 286 can desirably be such that the first fastening components 82 and 83 are positioned outward from and overlap the second fastening components 84 and 85 when the side panels 34 and 134 are fully extended and wrapped about the tubular body as shown in FIG. 17. The peripheral portions of the forming shoulders 300 and 330 can be separated, for example, by a distance of about 2 to about 20 millimeters. While folding the back side panels 134, the interior forming shoulder 300 can provide separation between the side panels and shield the second fastening components 84 and 85 from the first fastening components 82 and 83, thereby eliminating interference and premature engagement.

From the overlapping configuration illustrated in FIG. 17, a variety of fastener engagement mechanisms 253 can be used to refastenably or permanently bond the side panels 34 and 134 together. In the illustrated embodiment, the side panels 34 and 134 can be bonded together by causing contact between the fastening components 82–85. As shown in FIG. 18, the interior forming shoulder 300 can define a slot 318 that is positioned to coincide with the location of the fastening components 82–85. The slot 318 can allow the fastening components 82–85 to come into contact with one another after they have been positioned in an overlapping orientation. In one particular embodiment, a pair of opposing rollers 350 (FIGS. 11 and 18) can be mounted on opposite sides of the fastening components 82–85 to press the fastening components together. One set of rollers can be mounted on the downstream end 292 of the mandrel 285 and the opposing set of rollers can be mounted on the exterior forming shoulder flange 346. After the refastenable seams 88 are formed, the side panels 34 and 134 can be inspected if desired and allowed to pass beyond the downstream ends 292 of the cantilevered tubular bodies 286.

The fastener engagement mechanism 253 can rely on inertia, gravity, fluid blasts, mechanical devices such as rollers, wheels, registered or nonregistered driven discs or cones, or other suitable mechanisms to facilitate contact between the fastening components. Compressed air can be blown against the back side panel 134 to engage the fastening components 82–85, with the downstream end 292 of the mandrel 285 functioning as a backing surface to support the seam as the fasteners are engaged. Such engagement mechanisms can provide step-wise or progressive engagement of the fastening components.

An alternative exterior folding mechanism 252 can comprise a panel folding head (not shown) that is reciprocated into and out of the plane formed between the alignment conveyors 256 and 258 to intersect the path of travel of the back side panel 134 and move the back side panel into overlapping orientation with the front side panel 34. Such a panel folding head can move vertically into contact with the back side panel 134 and continue to move upward and push the back side panel 134 upward further. The back side panel 134 can contact and be folded around the mandrel 285 and the exterior surface 308 of the interior forming shoulder 300. The panel folding head can be connected either directly or indirectly to any suitable drive mechanism for moving the panel folding head so that the back side panel 134 overlaps the front side panel 34. The drive mechanism can comprise, for example, a four-bar linkage system including a pair of vertically-stacked rotatable discs, a connecting rod rotatively mounted at single points to each of the discs, and a motor for rotating the discs. The timing and rotation of the drive mechanism can be controlled to provide one complete cycle of the panel folding head for each training pant 102. Due to the orbital travel of the panel folding head, it can not only lift the back side panel, but can also carry it in the machine direction 108. The panel folding head can be coated to provide a positive gripping surface on the back side panel 134 while the side panel is carried into overlapping alignment with the front side panel 34. The drive mechanism can be configured so that, as the panel folding head achieves its maximum vertical position, the horizontal machine direction speed approximates the machine direction speed of the training pants 102.

Alternative refastenable or permanent bonding mechanisms can be employed to form either refastenable or permanent lap seams. Suitable permanent bonds can comprise ultrasonic bonds, thermal bonds, adhesive bonds or cohesive bonds. For ultrasonic or thermal bonds, by way of illustration, a cantilevered wheel can be mounted on the downstream end 292 of the mandrel 285 and an opposing ultrasonic or thermal bonding device can be mounted on the exterior forming shoulder flange 346. Alternative refastenable bonds can comprise various mechanical fasteners or refastenable adhesive bonds, or the like. For an adhesive bond, for example, adhesive may be applied to one or both pairs of side panels prior to being folded into an overlapping position.

The side panel seam forming apparatus can be easily adapted to select the desired amount of overlap of the side panels 34 and 134, for example, to accommodate different sizes and types of fastening components and/or different types of refastenable or permanent bonding mechanisms. The side panel seam forming apparatus can also accommodate front and back side panels of different widths, by changing the shape and/or orientation of the mandrel 285 and forming shoulders 300 and 330.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An apparatus for positioning a pair of panels in overlapping orientation, comprising:
    a transport system defining a machine center line;
    an interior panel folding mechanism adapted to position a first panel in an interior position, comprising:
        a mandrel transversely spaced from the machine center line and defining a curved peripheral surface, wherein the mandrel defines a body, an internal mandrel chamber within the body, and an aperture through the body and in communication with the internal chamber;
        an interior forming shoulder in proximity to the mandrel and defining an interior surface disposed toward the mandrel and an opposite exterior surface, the curved peripheral surface and the interior surface defining an inner passage therebetween; and
        a fluid pressure device operatively associated with the inner passage and adapted to establish an air flow through the inner passage; and
    an exterior panel folding mechanism adapted to position a second panel in an exterior position relative to the interior position.

2. The apparatus of claim 1, wherein the internal chamber is operatively connected to a source of vacuum.

3. The apparatus of claim 1, wherein the mandrel has a tubular shaped body aligned generally parallel with the machine center line.

4. The apparatus of claim 1, wherein the interior forming shoulder defines a distal edge, a head portion adjacent the distal edge, an upstream end and an opposite downstream end, and the interior forming shoulder is shaped such that the head portion is closer to the curved peripheral surface at downstream machine direction positions.

5. The apparatus of claim 1, wherein the interior forming shoulder increasingly curves around the mandrel at downstream machine direction positions.

6. The apparatus of claim 1, wherein the exterior panel folding mechanism is adapted to position the second panel against the exterior surface of the interior forming shoulder.

7. The apparatus of claim 1, wherein the exterior panel folding mechanism comprises:
    an exterior forming shoulder in proximity to the mandrel and defining an interior surface disposed toward the mandrel and defining an outer passage therebetween; and
    a fluid pressure device operatively associated with the outer passage and adapted to establish an air flow through the outer passage.

8. The apparatus of claim 7, wherein the exterior forming shoulder is positioned transversely outward from and overlaps the interior forming shoulder at particular machine direction positions.

9. The apparatus of claim 1, further comprising a fastener engagement mechanism adapted to refastenably bond fastening components of the first and second panels together.

10. An apparatus for positioning first and second panels in overlapping orientation, comprising:
    a transport system defining a machine center line;
    an interior panel folding mechanism adapted to position a first panel in an interior position, comprising:
        a mandrel transversely spaced from the machine center line and defining a curved peripheral surface;
        an interior forming shoulder defining an interior surface disposed toward the mandrel, an opposite exterior surface, a distal edge, and a head portion adjacent the distal edge and in contact with the mandrel, the curved peripheral surface and the interior surface defining an inner passage therebetween; and
        a fluid pressure device operatively associated with the inner passage and adapted to establish an air flow through the inner passage and against the interior surface; and
    an exterior panel folding mechanism adapted to position a second panel in an exterior position relative to the interior position.

11. The apparatus of claim 10, wherein the mandrel is a rigid structure.

12. The apparatus of claim 10, wherein the interior forming shoulder is a rigid structure.

13. The apparatus of claim 10, wherein the head portion is located closer to the mandrel at downstream machine direction position.

14. The apparatus of claim 10, wherein the fluid pressure device comprises a source of pressurized fluid adapted to expel fluid into the inner passage.

15. The apparatus of claim 10, wherein the air flow is directed generally transversely outward from the machine center line.

16. The apparatus of claim 10, wherein the interior forming shoulder and the curved peripheral surface are curved in the same direction.

17. The apparatus of claim 10, wherein the fluid pressure device comprises a source of vacuum operatively connected to the inner passage.

18. An apparatus for positioning first and second panels in overlapping orientation, comprising:
   a transport system defining a machine center line;
   an interior panel folding mechanism adapted to position a first panel in an interior position, comprising:
      a mandrel transversely spaced from the machine center line and defining a body having a curved peripheral surface, an internal mandrel chamber within the body, and an aperture through the body and in communication with the internal mandrel chamber;
      an interior forming shoulder in proximity to the mandrel and defining an interior surface disposed toward the mandrel and an opposite exterior surface, the curved peripheral surface and the interior surface defining an inner passage therebetween; and
      a fluid pressure device operatively associated with the inner passage and adapted to establish an air flow through the inner passage and into the internal mandrel chamber; and
   an exterior panel folding mechanism adapted to position a second panel in an exterior position relative to the interior position.

19. The apparatus of claim 18, wherein the mandrel is a rigid structure.

20. The apparatus of claim 18, wherein the interior forming shoulder is a rigid structure.

21. The apparatus of claim 18, wherein the interior forming shoulder defines a distal edge and a head portion adjacent the distal edge, the head portion being located closer to the mandrel at downstream machine direction positions.

22. The apparatus of claim 18, wherein the aperture comprises a slot having a length dimension aligned generally parallel with the machine center line.

23. The apparatus of claim 18, wherein the fluid pressure device comprises a source of pressurized fluid adapted to expel fluid into the inner passage.

24. The apparatus of claim 18, wherein the air flow is directed generally transversely outward from the machine center line.

25. The apparatus of claim 18, wherein the fluid pressure device comprises a source of vacuum operatively connected to the inner passage.

* * * * *